United States Patent
Akao et al.

(10) Patent No.: US 12,063,977 B2
(45) Date of Patent: Aug. 20, 2024

(54) POWER SUPPLY UNIT OF AEROSOL GENERATION DEVICE, CONTROL METHOD OF POWER SUPPLY UNIT OF AEROSOL GENERATION DEVICE, AND PROGRAM FOR POWER SUPPLY UNIT OF AEROSOL GENERATION DEVICE

(71) Applicant: JAPAN TOBACCO INC., Tokyo (JP)

(72) Inventors: Takeshi Akao, Tokyo (JP); Manabu Yamada, Tokyo (JP); Hiroshi Tezuka, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 781 days.

(21) Appl. No.: 17/236,457

(22) Filed: Apr. 21, 2021

(65) Prior Publication Data

US 2021/0235767 A1 Aug. 5, 2021

Related U.S. Application Data

(63) Continuation of application No. PCT/JP2019/039601, filed on Oct. 8, 2019.

(30) Foreign Application Priority Data

Oct. 30, 2018 (JP) ................................. 2018-203938
Oct. 30, 2018 (JP) ................................. 2018-203941

(51) Int. Cl.
*A24F 40/53* (2020.01)
*A24F 40/51* (2020.01)
(Continued)

(52) U.S. Cl.
CPC ............. *A24F 40/53* (2020.01); *A24F 40/51* (2020.01); *A24F 40/60* (2020.01);
(Continued)

(58) Field of Classification Search
CPC ......... A61M 15/06; A61M 2205/8206; H01M 10/425; H01M 2010/4271; A24F 40/60; A24F 40/53; A24F 40/51; A24F 40/57
See application file for complete search history.

(56) References Cited

U.S. PATENT DOCUMENTS

| | | | |
|---|---|---|---|
| 5,659,254 A | 8/1997 | Matsumoto et al. |
| 9,877,510 B2 | 1/2018 | Henry, Jr. |

(Continued)

FOREIGN PATENT DOCUMENTS

| | | |
|---|---|---|
| CN | 204682523 U | 10/2015 |
| CN | 205052868 U | 3/2016 |

(Continued)

OTHER PUBLICATIONS

International Search Report, issued in PCT/JP2019/039601, dated Dec. 17, 2019.

(Continued)

*Primary Examiner* — Marcus E Harcum
(74) *Attorney, Agent, or Firm* — Birch, Stewart, Kolasch & Birch, LLP

(57) ABSTRACT

In order to detect the occurrence of malfunction in a sensor, this power supply unit is provided with a microphone condenser which detects an aerosol generation request, a PTC thermistor which outputs a value which changes depending on electric change in the microphone condenser, and a control portion which, on the basis of the value outputted by the PTC thermistor, detects whether the microphone condenser is in a normal state or an abnormal state.

14 Claims, 15 Drawing Sheets

(51) Int. Cl.
    *A24F 40/60* (2020.01)
    *H01M 10/42* (2006.01)
    *A61M 15/06* (2006.01)
    *H02J 7/00* (2006.01)

(52) U.S. Cl.
    CPC ......... *H01M 10/425* (2013.01); *A61M 15/06* (2013.01); *A61M 2205/8206* (2013.01); *H01M 2010/4271* (2013.01); *H02J 7/0068* (2013.01)

(56) References Cited

U.S. PATENT DOCUMENTS

| | | | |
|---|---|---|---|
| 10,973,258 B2 * | 4/2021 | Alarcon | ............... A61M 15/06 |
| 2007/0068266 A1 | 3/2007 | Fujimori et al. | |
| 2009/0295558 A1 | 12/2009 | Kameyama | |
| 2011/0265806 A1 | 11/2011 | Alarcon et al. | |
| 2012/0100405 A1 | 4/2012 | Noda et al. | |
| 2013/0019887 A1 | 1/2013 | Liu | |
| 2014/0053856 A1 | 2/2014 | Liu | |
| 2014/0278250 A1 * | 9/2014 | Smith | ..................... A24F 40/51 |
| | | | 702/187 |
| 2015/0216233 A1 | 8/2015 | Sears et al. | |
| 2016/0128389 A1 | 5/2016 | Lamb et al. | |
| 2016/0366939 A1 | 12/2016 | Alarcon et al. | |
| 2017/0027234 A1 | 2/2017 | Farine et al. | |
| 2017/0258142 A1 | 9/2017 | Hatton et al. | |
| 2018/0042306 A1 * | 2/2018 | Atkins | ..................... A24F 40/50 |
| 2019/0033391 A1 | 1/2019 | Iwane et al. | |
| 2019/0247596 A1 * | 8/2019 | Freeman | ........... A61M 15/0001 |
| 2019/0247597 A1 | 8/2019 | Yamada et al. | |
| 2019/0247598 A1 | 8/2019 | Yamada et al. | |
| 2019/0380394 A1 | 12/2019 | Takeuchi et al. | |
| 2019/0380395 A1 | 12/2019 | Takeuchi et al. | |
| 2020/0337382 A1 * | 10/2020 | Sur | ........................ G06N 20/20 |

FOREIGN PATENT DOCUMENTS

| | | | | |
|---|---|---|---|---|
| CN | 106575877 A | * | 4/2017 | ............. A24F 40/40 |
| CN | 108338421 A | | 7/2018 | |
| JP | 8-15306 A | | 1/1996 | |
| JP | 2005-94885 A | | 4/2005 | |
| JP | 2007-86002 A | | 4/2007 | |
| JP | 2009-234437 A | | 10/2009 | |
| JP | 2009-294791 A | | 12/2009 | |
| JP | 2012-95433 A | | 5/2012 | |
| JP | 2013-186956 A | | 9/2013 | |
| JP | 2014-41834 A | | 3/2014 | |
| JP | 2016-118403 A | | 6/2016 | |
| JP | 2016-214258 A | | 12/2016 | |
| JP | 2017-511690 A | | 4/2017 | |
| JP | 2017-512480 A | | 5/2017 | |
| JP | 2017-514463 A | | 6/2017 | |
| JP | 2017-181206 A | | 10/2017 | |
| JP | 2017-535265 A | | 11/2017 | |
| JP | 3216735 U | | 6/2018 | |
| WO | WO 2018/138749 A1 | | 8/2018 | |
| WO | WO 2018/163261 A1 | | 9/2018 | |
| WO | WO 2018/163262 A1 | | 9/2018 | |

OTHER PUBLICATIONS

Japanese Office Action for Japanese Application No. 2019-139691 dated Nov. 4, 2022, with English translation.
Japanese Notice of Reasons for Refusal for Japanese Application No. 2023-079066, dated Jul. 4, 2023, with English translation.
Extended European Search Report for European Application No. 19880189.6, dated Jun. 29, 2022.
Japanese Office Action for Japanese Application No. 2019-139691, dated Feb. 13, 2023, with an English translation.
Japanese Office Action for corresponding Japanese Application No. 2023-179368, dated Dec. 7, 2023, with English translation.
Japanese Notice of Reasons for Refusal for Japanese Application No. 2023-179368, dated Feb. 13, 2024, with an English translation.

* cited by examiner

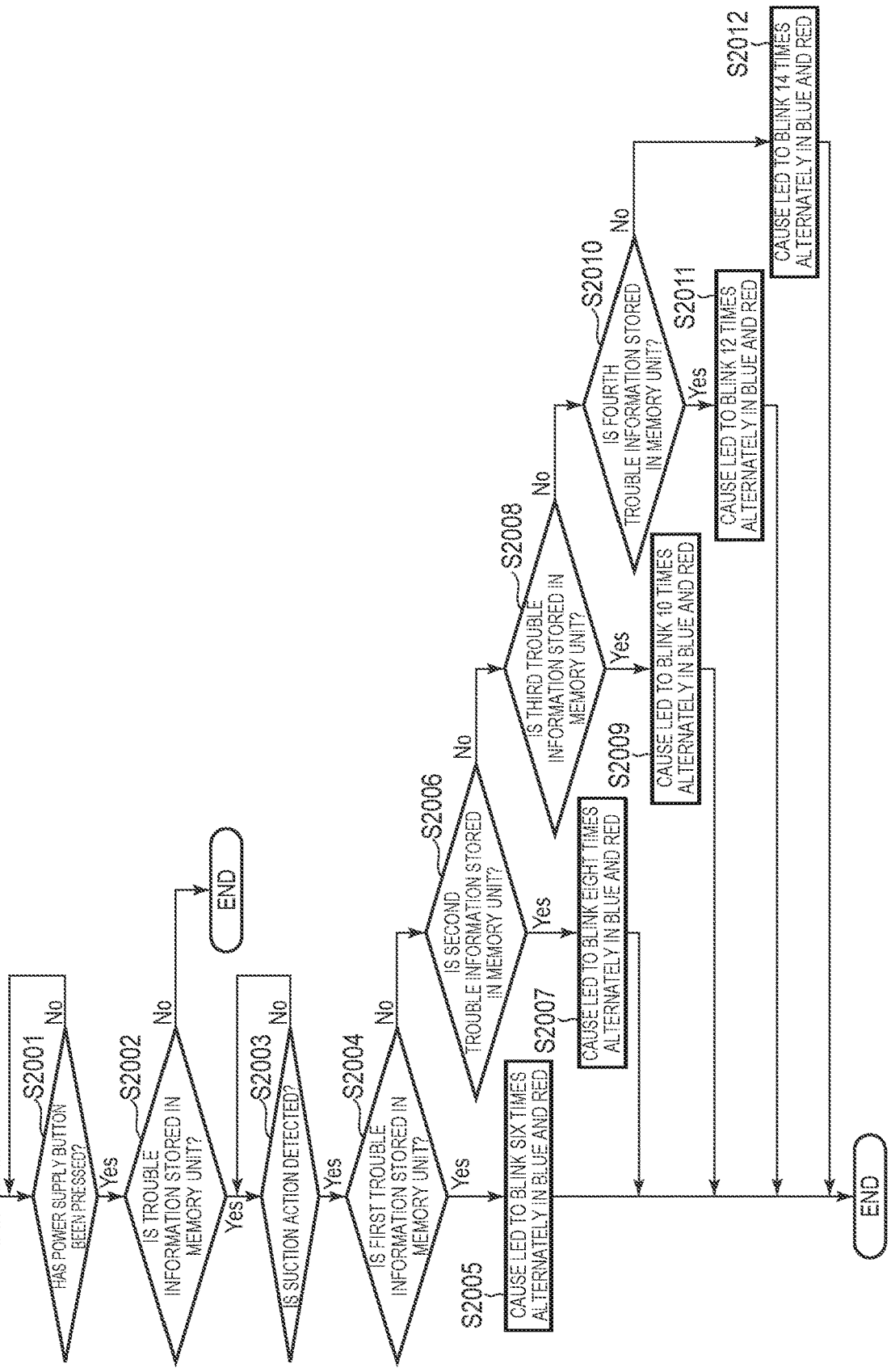

POWER SUPPLY UNIT OF AEROSOL GENERATION DEVICE, CONTROL METHOD OF POWER SUPPLY UNIT OF AEROSOL GENERATION DEVICE, AND PROGRAM FOR POWER SUPPLY UNIT OF AEROSOL GENERATION DEVICE

CROSS REFERENCE TO RELATED APPLICATIONS

This application is a Continuation of PCT International Application No. PCT/JP2019/039601, filed on Oct. 8, 2019, which claims priority under 35 U.S.C. 119(a) to Patent Application Nos. 2018-203938 and 2018-203941, filed in Japan on Oct. 30, 2018, all of which are hereby expressly incorporated by reference into the present application.

TECHNICAL FIELD

The present invention relates to a power supply unit of an aerosol generation device, a control method of the power supply unit of the aerosol generation device, and a program for the power supply unit of the aerosol generation device.

BACKGROUND ART

An aerosol generation device is known with which a user can taste aerosol generated by atomizing an aerosol source with an electric load such as a heater.

PTL 1 discloses a technique of supplying electric power to a heater when a user's suction action is detected based on an output of a sensor that measures an amount of air flowing in the device.

PTL 2 discloses a technique of adjusting a value of electric power to be supplied to a heater based on an output of a sensor that measures a flow rate of air flowing in the device.

A power supply such as a battery serving as a power source is built in the above-described aerosol generation device, in many cases.

As a technique related to the aerosol generation device, a technique of notifying that a remaining amount of the power supply has decreased, or the like, using a light emitting diode (LED) or the like is known.

PTL 3 discloses a technique of activating an indicator that notifies that a power supply requires replacement when a power supply voltage becomes lower than a threshold voltage.

PTL 4 discloses a technique of adjusting the luminous intensity of illumination and the like based on an electrical power source level.

PTL 5 discloses a technique of causing a light-emitting element to emit light when an electronic cigarette is used for smoking.

PTL 6 discloses a technique of causing an LED to emit light in different colors according to a remaining amount of a power supply.

CITATION LIST

Patent Literature

PTL 1: Japanese Translation of PCT International Application Publication No. 2017-535265
PTL 2: Japanese Translation of PCT International Application Publication No. 2017-512480
PTL 3: Japanese Translation of PCT International Application Publication No. 2017-514463
PTL 4: Japanese Translation of PCT International Application Publication No. 2017-511690
PTL 5: U.S. Unexamined Patent Application Publication No. 2013/0019887
PTL 6: Chinese Utility Model Laid-Open No. 204682523

SUMMARY OF INVENTION

Technical Problem

When the aerosol generation device continues to be used, a sensor that detects a user's suction action may have a trouble due to deterioration over time. When the sensor has such a trouble, the aerosol source is atomized by the aerosol generation device without user's intention, for example, when the user does not perform the suction action, whereby the aerosol source may be wasted. Therefore, in the case where the trouble has occurred in the sensor, it is desired to detect such occurrence of trouble.

However, the techniques disclosed in PTLs 1 and 2 are techniques of controlling the supply of electric power to the heater according to an output value of the sensor, and do not reflect detecting the trouble in the sensor.

The present invention has been made in view of the above circumstances, and has a first object to provide a power supply unit of an aerosol generation device capable of detecting occurrence of a trouble in a sensor, a control method for a power supply unit of the aerosol generation device, and a program for the power supply unit of the aerosol generation device.

When the aerosol generation device continues to be used, a power supply may have a trouble due to deterioration over time. To perform repairs to solve such a trouble, it is necessary to recognize the content or cause of the trouble. To recognize the content or cause of the trouble, various inspections are required to be performed, which may take a lot of time and labor. Therefore, there is desired a technique capable of easily recognizing the content or cause of the trouble that has occurred in the power supply.

The present invention has been made in view of the above circumstances, and has a second object to provide a power supply unit of an aerosol generation device capable of easily recognizing a content or a cause of a trouble that has occurred in a power supply, a control method for the aerosol generation device, a program, and a power supply unit of an inhaler.

Solution to Problem

A power supply unit of an aerosol generation device according to a first embodiment of the present invention includes a first sensor configured to detect an aerosol generation request, a second sensor configured to output a value in the second sensor that changes according to an electrical change of the first sensor, and a control unit configured to detect, based on the value, whether the first sensor is in a normal state or an abnormal state.

The value when the control unit detects the normal state may be different from the value when the control unit detects the abnormal state.

Furthermore, the abnormal state may be a state in which an aerosol source is not atomized by an atomization unit to which electric power is supplied from the power supply unit, due to a trouble occurring in the first sensor.

The normal state may be a state in which an aerosol source is capable of being atomized by an atomization unit to which electric power is supplied from the power supply unit.

Furthermore, a value output from the second sensor is a value of a voltage applied to the second sensor that changes according to a change in a voltage applied to the first sensor, and the control unit may be configured to detect, based on the voltage value, whether the first sensor is in the normal state or the abnormal state.

The second sensor may be a PTC thermistor.

Furthermore, a value output from the second sensor is a value of a current flowing in the second sensor that changes according to a change in a current flowing in the first sensor, and the control unit may be configured to detect, based on the current value, whether the first sensor is in the normal state or the abnormal state.

The power supply unit further includes a notification unit, and when detecting the abnormal state, the control unit may be configured to cause the notification unit to make a notification that the abnormal state is detected.

When the abnormal state is detected, the control unit may be configured to cause the power supply unit to undergo a transition from an active state to a sleep state.

The power supply unit further includes a memory unit, and the memory unit may be configured to store information indicating the number of times that the control unit has detected the abnormal state.

The memory unit may be configured to further store information indicating a content of the abnormal state detected by the control unit.

When detecting an instruction to cause the power supply unit to undergo a transition to an active state, the control unit may be configured not to cause the power supply unit to undergo a transition to an active state when the number of times is equal to or greater than a predetermined threshold, and to cause the power supply unit to undergo the transition to the active state when the number of times is less than the predetermined threshold.

When the power supply unit is in an active state, the control unit may be configured to detect whether the first sensor is in the normal state or the abnormal state.

A control method for a power supply unit of an aerosol generation device according to a first embodiment of the present invention includes the steps of acquiring a value in a second sensor that changes according to an electrical change of a first sensor that detects an aerosol generation request, and detecting, based on the value, whether the first sensor is in a normal state or an abnormal state.

A program for a power supply unit of an aerosol generation device according to a first embodiment of the present invention causes a computer to execute processes of acquiring a value in a second sensor that changes according to an electrical change of a first sensor that detects an aerosol generation request, and detecting, based on the value, whether the first sensor is in a normal state or an abnormal state.

A power supply unit of an aerosol generation device according to a second embodiment of the present invention includes a power supply, a notification unit, and a control unit configured to determine whether the power supply is in a normal state or a trouble state based on an operation value related to an operation of the power supply, and when the trouble state is detected, cause the notification unit to make a notification corresponding to a type of the trouble state at a first timing, and cause the notification unit to make a notification corresponding to a type of the trouble state at a second timing that is a timing when a user's suction action is detected or when the aerosol generation device undergoes a transition to an active state.

The trouble state may include a plurality of trouble states. The control unit may generate a plurality of types of error signals corresponding to the plurality of trouble states.

The control unit may cause the notification unit to make a notification in a mode corresponding to the type of the error signal.

The control unit may cause the notification unit to emit light in a mode corresponding to the type of the error signal.

The control unit may cause the notification unit to generate a vibration in a mode corresponding to the type of the error signal.

The control unit may cause the notification unit to generate a sound in a mode corresponding to the type of the error signal.

When the trouble state is detected, the control unit may cause the notification unit to make a notification about the trouble state at a plurality of timings.

The first timing may be when the trouble state is detected. The second timing may be after the trouble state is detected.

The number of elements in the power supply unit to which electric power is to be supplied from the power supply at the first timing may be greater than the number of elements in the power supply unit to which the electric power is to be supplied from the power supply at the second timing.

The second timing may be a timing of detecting an instruction to cause the aerosol generation device to undergo a transition to a power supply on state.

The second timing may be a timing of detecting the suction action by a sensor unit.

The control unit may control so that power consumption required for a notification about the trouble state at the second timing is smaller than the power consumption required for a notification about the trouble state at the first timing.

The trouble state may include a plurality of trouble states, and importance may be set for each of the plurality of trouble states. With respect to the trouble state with the importance lower than a predetermined level, the control unit may cause the notification unit to make a notification about the trouble state only at the first timing.

The trouble state may include a plurality of trouble states, and importance may be set for each of the plurality of trouble states. The power consumption may be increased for a notification about the trouble state with higher importance.

The trouble state may include a plurality of trouble states, and importance may be set for each of the plurality of trouble states. The control unit may change a mode of the notification according to the importance set for the trouble state.

The operation value may include a voltage value of the power supply. When detecting, based on the operation value, that an amount of decrease per a predetermined time period of the voltage value of the power supply is equal to or greater than a first threshold during charging of the power supply, the control unit may determine that the power supply is in the trouble state.

The operation value may include a voltage value of the power supply. When detecting, based on the operation value, that a time period required for the voltage value of the power supply to increase from a lower limit to an upper limit of a first voltage range is equal to or less than a second threshold during charging of the power supply, the control unit may determine that the power supply is in the trouble state. The first voltage range may be included in a voltage range equal to or greater than a discharge termination voltage of the power supply.

The operation value may include a voltage value of the power supply. When detecting, based on the operation value, that a time period required for the voltage value of the power supply to increase from a lower limit to an upper limit of a second voltage range is equal to or greater than a third threshold during charging of the power supply, the control unit may determine that the power supply is in the trouble state. The second voltage range may be included in a voltage range less than a discharge termination voltage of the power supply.

The operation value may include a total charging time period of the power supply. When detecting, based on the operation value, that the total charging time period of the power supply is equal to or greater than a fourth threshold, the control unit may determine that the power supply is in the trouble state.

The operation value may include a temperature of the power supply. When detecting, based on the operation value, that the temperature of the power supply is equal to or higher than a fifth threshold, the control unit may determine that the power supply is in the trouble state.

The control unit may cause the notification unit to make a notification that an internal short circuit has occurred in the power supply when detecting that the amount of decrease per a predetermined time period of the voltage value of the power supply is equal to or greater than the first threshold during charging of the power supply, cause the notification unit to make a notification that a capacity of the power supply has deteriorated when detecting that the time period required for the voltage value of the power supply to increase from the lower limit to the upper limit of the first voltage range is equal to or less than the second threshold during charging of the power supply, cause the notification unit to make a notification that deterioration due to overdischarge has occurred in the power supply when detecting that the time period required for the voltage value of the power supply to increase from the lower limit to the upper limit of the second voltage range is equal to or greater than the third threshold during charging of the power supply, cause the power supply part to make a notification that the power supply has reached an end of a lifespan when detecting that the total charging time period of the power supply is equal to or greater than the fourth threshold, and cause the notification unit to make a notification that a temperature abnormality has occurred in the power supply when detecting that the temperature of the power supply is equal to or higher than the fifth threshold.

When determining that the power supply is in the trouble state, the control unit may inhibit charging or discharging of the power supply.

The trouble state may include a state in which the power supply is deteriorated and/or a state in which the power supply fails.

A control method for an aerosol generation device according to a second embodiment of the present invention includes the steps of determining whether the power supply is in a normal state or a trouble state based on an operation value related to an operation of a power supply, and when the trouble state is detected, making a notification corresponding to a type of the trouble state at a first timing, and making a notification corresponding to a type of the trouble state at a second timing that is a timing when a user's suction action is detected or when the aerosol generation device undergoes a transition to an active state.

A program according to a second embodiment of the present invention causes a computer to execute processes of determining whether the power supply is in a normal state or a trouble state based on an operation value related to an operation of a power supply, and when the trouble state is detected, making a notification corresponding to a type of the trouble state at a first timing, and making a notification corresponding to a type of the trouble state at a second timing that is a timing when a user's suction action is detected or when the aerosol generation device undergoes a transition to an active state.

A power supply unit of an inhaler according to a second embodiment of the present invention includes a power supply, a notification unit, and a control unit configured to determine whether the power supply is in a normal state or a trouble state based on an operation value related to an operation of the power supply, and when the trouble state is detected, cause the notification unit to make a notification corresponding to a type of the trouble state at a first timing, and cause the notification unit to make a notification corresponding to a type of the trouble state at a second timing that is a timing when a user's suction action is detected or when the inhaler undergoes a transition to an active state.

Advantageous Effects of Invention

According to a power supply unit of an aerosol generation device according to a first embodiment of the present invention, a control method for a power supply unit of the aerosol generation device, and a program for the power supply unit of the aerosol generation device, the occurrence of a trouble in a sensor can be detected.

According to a power supply unit of an aerosol generation device according to a second embodiment of the present invention, a control method for the aerosol generation device, a program, and a power supply unit of an inhaler, a content or a cause of a trouble that has occurred in a power supply can be easily recognized.

BRIEF DESCRIPTION OF DRAWINGS

FIG. 20 is a flowchart illustrating an example of a notification process of first to fifth trouble states while a user's suction action is performed.

DESCRIPTION OF EMBODIMENTS

Hereinafter, embodiments of the present invention will be described with reference to the drawings. Note that in the following description, approximately or substantially the same functions and constituent elements are denoted by the same reference signs, and are described only when necessary.

First Embodiment

In the following description, it is assumed that an aerosol generation device 1 according to the present embodiment is, for example, a heated cigarette or an electronic cigarette. However, the aerosol generation device 1 according to the present embodiment may be an aerosol generation device of another type or usage, such as a nebulizer.

Figure 1:
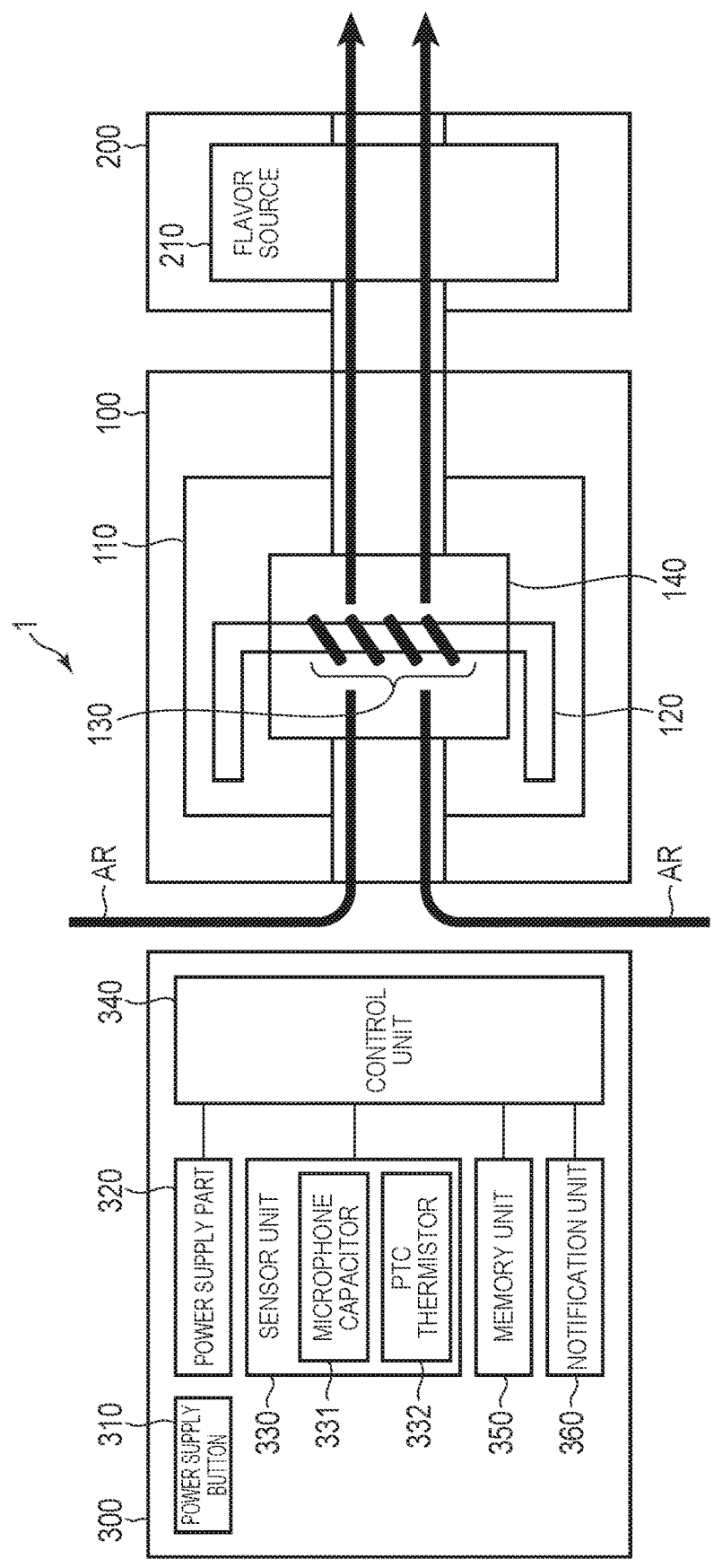
FIG. 1 is a block diagram illustrating an example of a schematic configuration of an aerosol generation device according to a first embodiment of the present invention.

FIG. 1 is a block diagram illustrating an example of a schematic configuration of the aerosol generation device 1 according to the present embodiment.

As illustrated in FIG. 1, the aerosol generation device 1 includes a cartridge unit 100, a capsule unit 200, and a power supply unit 300. The aerosol generation device 1 is configured, for example, in a substantially cylindrical shape, so that a user can easily hold the aerosol generation device 1.

Note that the cartridge unit 100, the capsule unit 200, and the power supply unit 300 may be configured to be connected to one another in a non-detachable or detachable manner.

As illustrated in FIG. 1, the cartridge unit 100 includes a storage unit 110, a supply unit 120, and an atomization unit 140 provided with a load 130.

The storage unit 110 is a container for storing a liquid aerosol source to be atomized through heating. The aerosol source is, for example, a polyol-based material such as glycerin or propylene glycol. The aerosol source may also be a liquid mixture that contains a nicotine liquid, water, a flavoring agent, etc. Alternatively, the aerosol source may also be a solid for which the storage unit 110 is unnecessary.

The supply unit 120 is, for example, a wick that is formed by twisting a fiber material such as glass fibers. One end of the supply unit 120 is connected to the storage unit 110. The other end of the supply unit 120 is connected to the load 130 or is arranged in the vicinity of the load 130. With such an arrangement, the supply unit 120 can soak up the aerosol source from the storage unit 110 and guide the aerosol source to the load 130 or the vicinity of the load 130. Note that the wick made of porous ceramic may also be used for the supply unit 120.

The load 130 provided in the atomization unit 140 is a coil-shaped heater, for example, and generates heat when the electric power is supplied thereto. The load 130 may be wound around the supply unit 120 or may be covered by the supply unit 120. The electric power is supplied to the load 130 from a power supply part 320, which will be described later, based on the control by a control unit 340, which will be described later, included in the power supply unit 300. When the electric power is supplied to the load 130, the aerosol source guided by the supply unit 120 is heated by the load 130, whereby aerosol is generated.

The capsule unit 200 includes a flavor source 210, as illustrated in FIG. 1.

The flavor source 210 includes a raw material piece of a plant material that imparts a flavor component to the aerosol. For example, shredded tobacco or a forming body obtained by forming a tobacco material such as a tobacco raw material in a granular form or a sheet form is used as the raw material piece which is a component of the flavor source. In addition, a plant (for example, mint, a herb, or the like) other than tobacco may be used as the raw material piece which is a component of the flavor source 210. The flavor source 210 may be provided with a flavor such as menthol.

Each arrow in FIG. 1 indicates the flow of air in the cartridge unit 100 and the capsule unit 200. The air taken in from the outside through an air intake opening (not illustrated) is mixed with the aerosol in the process of passing through the aerosol generation device 1 (the cartridge unit 100 and the capsule unit 200) to which a flavor component is added, and the resultant mixture is sucked by the user. Specifically, the air taken in from the outside passes through the atomization unit 140 in the cartridge unit 100. While passing through the atomization unit 140, the air is mixed with the aerosol generated by the load 130 provided in the atomization unit 140. Then, when the air mixed with the aerosol passes through the capsule unit 200, the flavor component derived from the flavor source 210 included in the capsule unit 200 is added to the air mixed with the aerosol. Then, the air mixed with the aerosol and added with the flavor component is sucked by the user from the end portion of the capsule unit 200. That is, the aerosol to which the flavor component is added is sucked by the user.

As illustrated in FIG. 1, the power supply unit 300 includes a power supply button 310, the power supply part 320, a sensor unit 330, the control unit 340, a memory unit 350, and a notification unit 360.

The power supply button 310 is a button for causing an operating state transition of the aerosol generation device 1. When the power supply button 310 is pressed to turn on the power supply, the aerosol generation device 1 undergoes the transition to an active state, which will be described later. When the power supply button 310 is pressed to turn off the power supply while the aerosol generation device 1 is in the active state, the aerosol generation device 1 undergoes the transition from the active state to a sleep state, which will be described later.

Note that saying that the aerosol generation device 1 is in the active state is equivalent to saying that the battery unit 300 is in the active state. Moreover, saying that the aerosol generation device 1 is in the sleep state is equivalent to saying that the battery unit 300 is in the sleep state.

The power supply part 320 is, for example, a rechargeable battery such as a lithium-ion secondary battery, and its type is not limited. The power supply part 320 supplies the electric power to each portion of the aerosol generation device 1 based on the control by the control unit 340.

The sensor unit 330 has at least a function of detecting a user's suction action (an action for requesting the aerosol generation device 1 to generate the aerosol) and a function of detecting troubles of the detection function and the like. As illustrated in FIG. 1, the sensor unit 330 includes a microphone capacitor 331 which is a first sensor, and a positive temperature coefficient (PTC) thermistor 332 which is a second sensor. The microphone capacitor 331 detects the user's suction action.

The PTC thermistor 332 has a function of preventing an excessive current from flowing in each element and the like that constitutes the sensor unit 330 (hereinafter, referred to as an "overcurrent protection function") before the excessive current flows therein.

Note that the sensor unit 330 will be described in detail later.

The control unit 340 causes the aerosol generation device 1 to undergo the transition to one of two operating states when the power supply button 310 is pressed. The two operating states include an active state in which the electric power can be supplied from the power supply part 320 to each portion of the aerosol generation device 1 and a sleep state in which no electric power can be supplied from the power supply part 320 to each portion of the aerosol generation device 1 or only minimal electric power can be supplied from the power supply part 320 to each portion of the aerosol generation device 1. When the sensor unit 330 detects the user's suction action while the aerosol generation device 1 is in the active state, the control unit 340 causes the power supply part 320 to supply the electric power to the load 130 to atomize the aerosol source. When the power supply unit 300 is in the sleep state, the control unit 340 does not cause the power supply part 320 to supply the electric power to the load 130 even when the user performs a suction action. Therefore, the aerosol source is not atomized. Note that the electric power is supplied from the power supply part 320 to the load 130 under the control by the control unit 340 while the sensor unit 330 detects the user's suction action.

The control unit 340 detects whether the microphone capacitor 331 is in a normal state or an abnormal state, based on a voltage value applied to the PTC thermistor 332.

Here, the normal state refers to a state in which the microphone capacitor 331 has no trouble and can normally detect the user's suction action. In other words, the normal state refers to a state in which when the user performs the suction action, the microphone capacitor 331 detects such a suction action, and the electric power is supplied to the load 130, whereby the aerosol is generated.

The abnormal state refers to a state in which the microphone capacitor 331 has a trouble, and cannot normally detect the user's suction action. In other words, the abnormal state refers to a state in which even when the user performs the suction action, the microphone capacitor 331 does not detect such a suction action, and therefore no aerosol is generated. In addition, the abnormal state refers to a state in which the microphone capacitor 331 detects the user's suction action even though the user does not perform the suction action, and the electric power is supplied to the load 130, whereby the aerosol is generated.

Note that after the power supply button 310 is pressed and the aerosol generation device 1 undergoes the transition from the sleep state to the active state, the control unit 340 always performs a process of detecting whether the microphone capacitor 331 is in the normal state or the abnormal state (hereinafter, referred to as a "state detection process"). In addition, when the power supply button 310 is pressed and the power supply unit 300 undergoes the transition from the active state to the sleep state, the control unit 340 does not perform the state detection process. The state detection process will be described in detail later.

The memory unit 350 is, for example, a non-volatile memory. The memory unit 350 stores various types of data and programs for operating the aerosol generation device 1. The memory unit 350 stores a program (or firmware) for executing the state detection process, for example.

In addition, when the control unit 340 detects that the sensor unit 330 (in particular, the microphone capacitor 331) is in an abnormal state, the memory unit 350 stores information on the abnormal state. Specifically, the memory unit 350 stores the content of the trouble that has occurred in the sensor unit 330.

Furthermore, the memory unit 350 stores the number of times that the control unit 340 has detected that the microphone capacitor 331 is in the abnormal state (hereinafter, referred to as the "number of times of detection") and a limit threshold that is a value limiting the state transition of the aerosol generation device 1 from the sleep state to the active state. The number of times of detection and the limit threshold will be described in detail later.

The notification unit 360 is, for example, a light emitting diode. The notification unit 360 emits light based on the control by the control unit 340. For example, when the control unit 340 detects that the microphone capacitor 331 is in the abnormal state, the notification unit 360 emits light under the control by the control unit 340. Examples of the color of light emitted from the notification unit 360 can include, but not particularly limited to, a cold (bluish) color, a warm (reddish) color, and the like.

Note that the notification unit 360 may be provided, for example, along the circumferential direction of the upstream end of the power supply unit 300 and installed so that the entire end may emit light. Furthermore, for example, the notification unit 360 may be provided along the circumferential direction of the power supply button 310 and installed so that the periphery of the power supply button 310 emits light.

Next, the sensor unit 330 will be described in detail.

Figure 2:
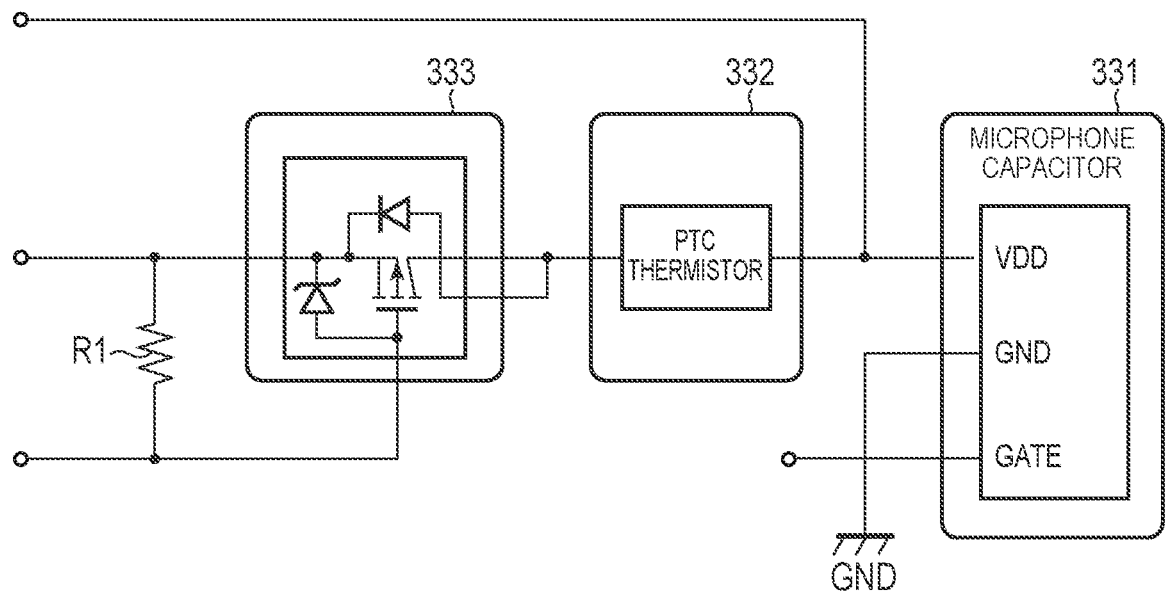
FIG. 2 is a diagram illustrating an example of a circuit configuration of a sensor unit according to the first embodiment of the present invention.

FIG. 2 is a diagram illustrating an example of a circuit configuration of the sensor unit 330. As illustrated in FIG. 2, the circuit includes the microphone capacitor 331, the PTC thermistor 332, and a P-type MOSFET 333. When the power supply button 310 is pressed and the aerosol generation device 1 undergoes the transition from the sleep state to the active state, the base voltage is applied and the drain current flows in the P-type MOSFET 333. Then, the current flows through the PTC thermistor 332 and the microphone capacitor 331, and the PTC thermistor 332 and the microphone capacitor 331 are brought into a state in which they can perform the respective functions.

Figure 3:
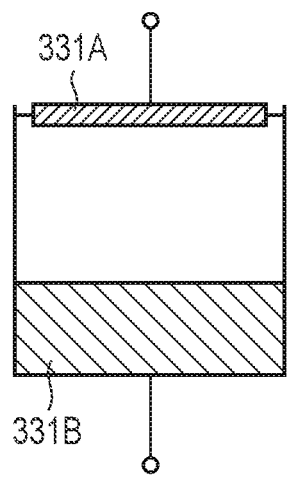
FIG. 3 is a diagram illustrating an example of a configuration of a microphone capacitor according to the first embodiment of the present invention.

FIG. 3 is a diagram illustrating an example of a configuration of the microphone capacitor 331.

The microphone capacitor 331 includes a diaphragm 331A that is a metal plate made to vibrate by changes in sound and pressure due to the user's suction action, and a back plate 331B that is a fixed metal plate. The electrostatic capacitance defined by the diaphragm 331A and the back plate 331B does not change when there are no changes in sound and pressure due to the user's suction action. On the other hand, when there are changes in sound and pressure due to the user's suction action, the diaphragm 331A vibrates based on the changes in sound and pressure, and the electrostatic capacitance defined by the diaphragm 331A and the back plate 331B changes. The user's suction action is detected based on the change in the electrostatic capacitance.

Figure 4:
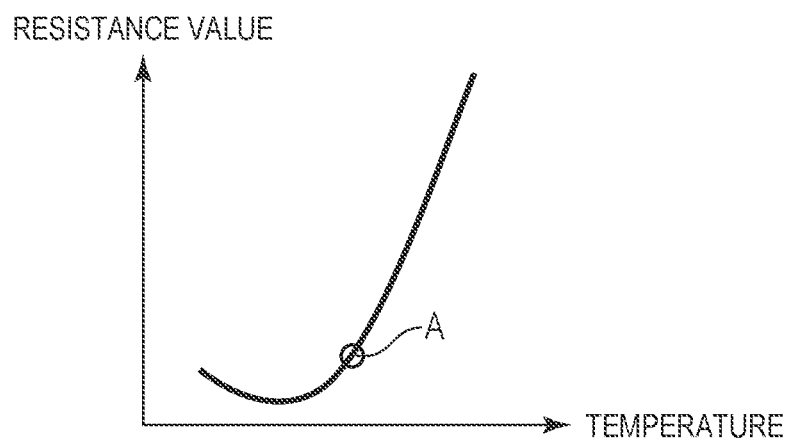
FIG. 4 is a graph showing an example of a resistance-temperature characteristic of a PTC thermistor according to the first embodiment of the present invention.
Figure 5:
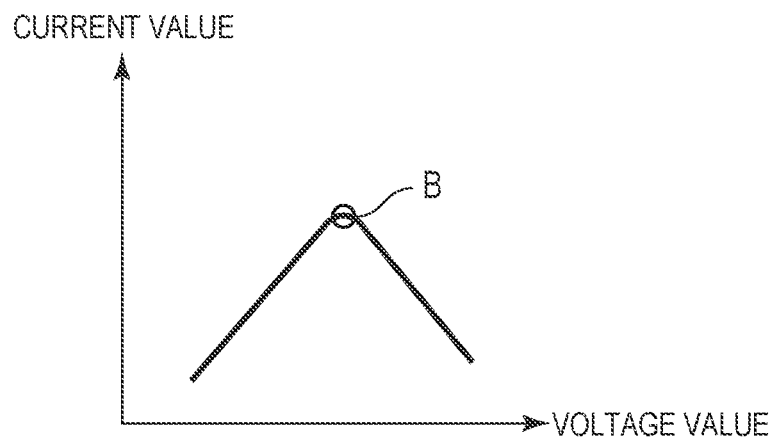
FIG. 5 is a graph showing an example of a voltage-current characteristic of the PTC thermistor according to the first embodiment of the present invention.

FIGS. 4 and 5 each are a graph showing characteristics of the PTC thermistor 332.

FIG. 4 shows an example of a resistance-temperature characteristic of the PTC thermistor 332, where the vertical axis represents a resistance value and the horizontal axis represents a temperature. As shown in FIG. 4, the resistance value of the PTC thermistor 332 is a substantially constant value when the temperature of the PTC thermistor 332 is low (for example, about room temperature), but increases sharply when exceeding a predetermined value (hereinafter, referred to as a "point A"). Therefore, when the temperature of the PTC thermistor 332 becomes equal to or higher than the temperature at the point A, the PTC thermistor 332 functions to prevent the excessive current from flowing. That is, the PTC thermistor 332 performs the overcurrent protection function.

FIG. 5 shows an example of a voltage-current characteristic of the PTC thermistor 332, where the vertical axis represents a current value and the horizontal axis represents a voltage value. As shown in FIG. 5, in the PTC thermistor 332, the current value also increases proportionally up to a certain voltage value according to Ohm's law, but since the resistance value increases suddenly when the voltage value exceeds a certain voltage value (hereinafter, referred to as a "point B"), the current value decreases. In other words, when the voltage vale applied to the PTC thermistor 332 reaches a value exceeding the point B, the PTC thermistor 332 functions to prevent an excessive current from flowing. That is, the PTC thermistor 332 performs the overcurrent protection function.

As illustrated in FIG. 3, since the PTC thermistor 332 is electrically connected to the microphone capacitor 331, the voltage value applied to the PTC thermistor 332 is affected by the electrical change in the microphone capacitor 331. Therefore, the fact that the voltage value of the PTC thermistor 332 reaches a value exceeding the point B means that the microphone capacitor 331 has a trouble in that the excessive current tries to flow. Such a trouble is in that a short circuit has occurred in the microphone capacitor 331, for example. In addition, the electrical change in the microphone capacitor 331 affects a change in voltage value applied to the microphone capacitor 331, a change in the current value flowing in the microphone capacitor 331, and the like.

In the present embodiment, the control unit 340 acquires the voltage value applied to the PTC thermistor 332 based on an output from the PTC thermistor 332, for example. Then, the control unit 340 compares the voltage value with a preset voltage threshold equal to or higher than the point B, and detects whether the microphone capacitor 331 is in the normal state or the abnormal state. Specifically, when the voltage value applied to the PTC thermistor 332 is equal to or higher than the above-described voltage threshold, the control unit 340 detects that the microphone capacitor 331 is in the abnormal state. That is, the control unit 340 detects that the microphone capacitor 331 has the trouble (a short circuit).

Figure 6:
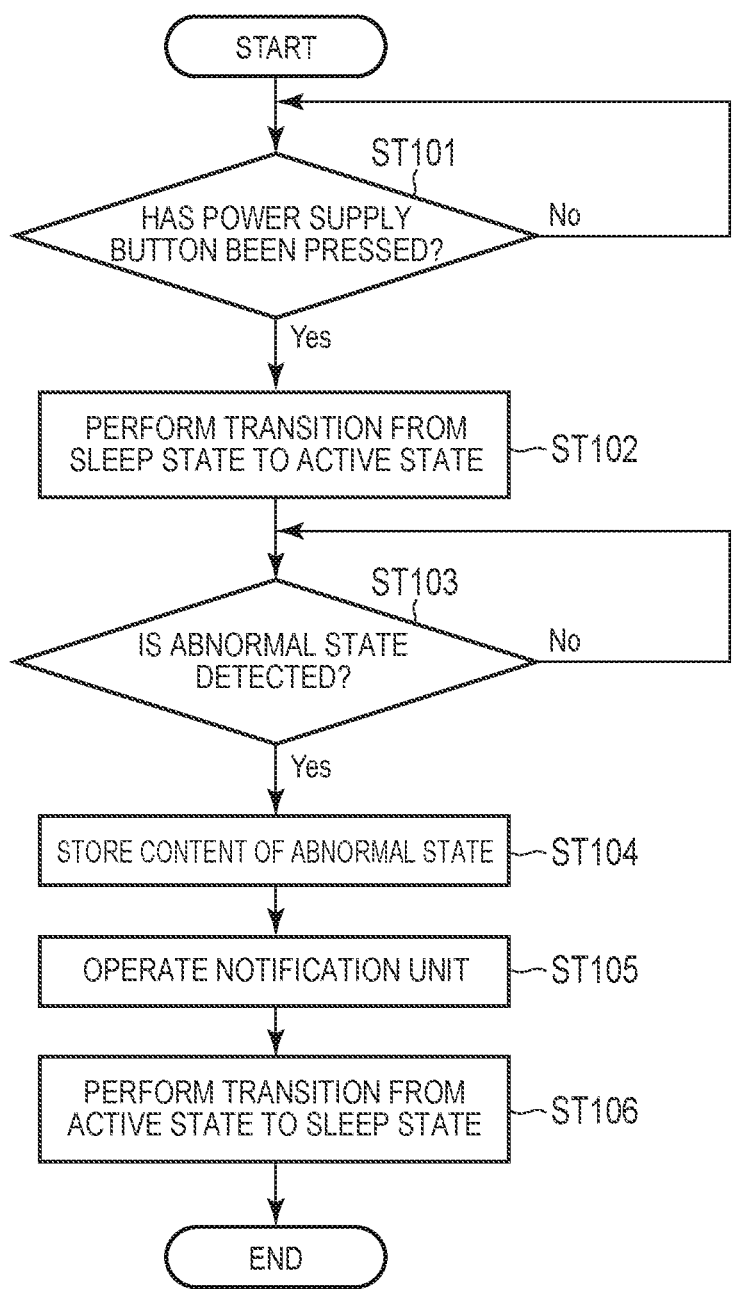
FIG. 6 is a flowchart illustrating an example of a state detection process according to the first embodiment of the present invention.
Figure 7:
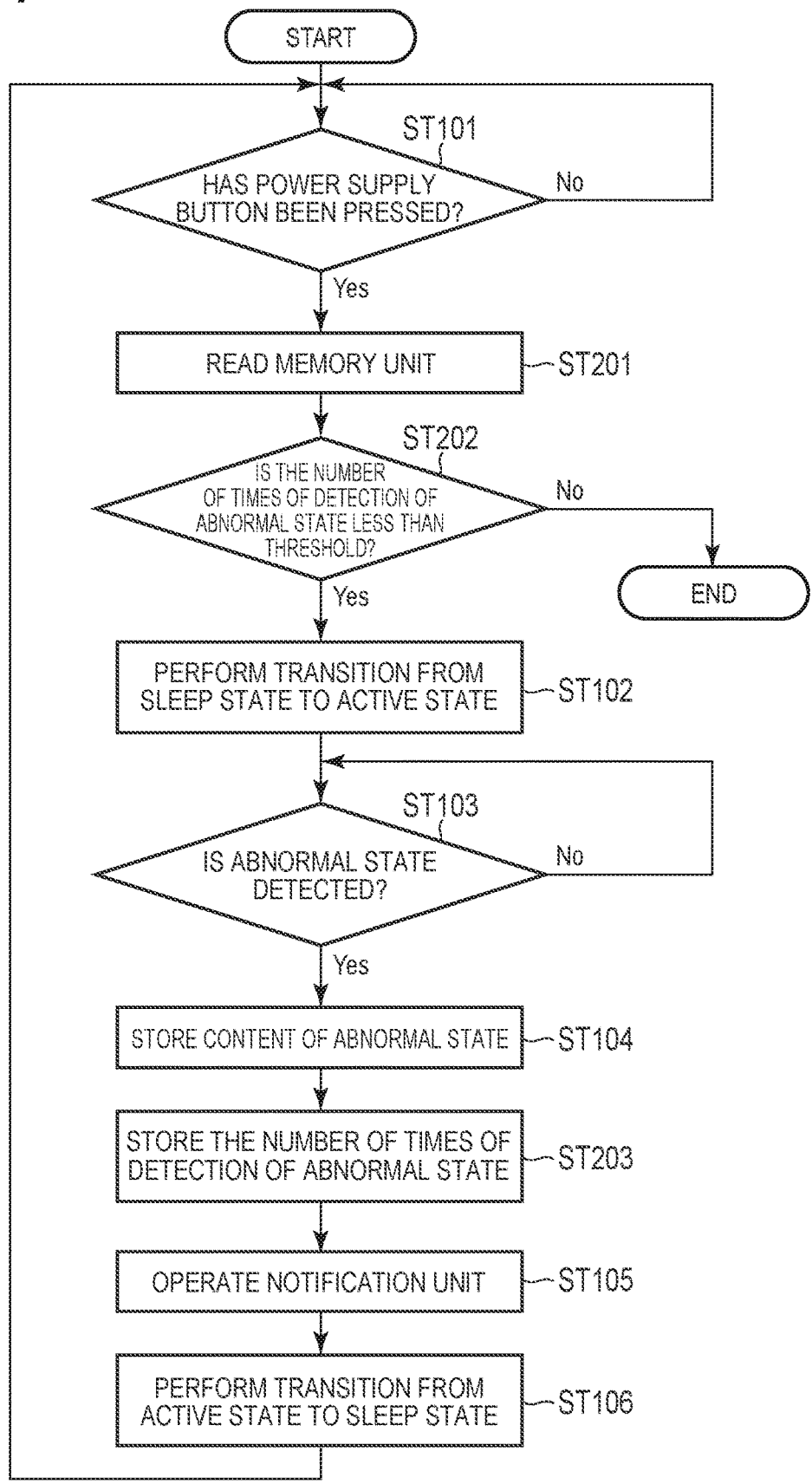
FIG. 7 is a flowchart illustrating another example of the state detection process according to the first embodiment of the present invention.

Next, the state detection process to be performed by the control unit 340 will be described in detail. FIG. 6 is a flowchart illustrating an example of the state detection process to be performed by the control unit 340.

The control unit 340 determines whether the power supply button 310 has been pressed while the aerosol generation device 1 is in the sleep state (ST101). When the control unit 340 does not determine that the power supply button 310 has been pressed (ST101: NO), the process in step ST101 is performed again. That is, the aerosol suction device 1 is in the sleep state until the power supply button 310 is pressed.

When determining that the power supply button 310 has been pressed (ST101: YES), the control unit 340 causes the aerosol generation device 1 to undergo the transition from the sleep state to the active state (ST102).

Then, the control unit 340 detects whether the microphone capacitor 331 is in the abnormal state (ST103). As described above, the control unit 340 detects whether the microphone capacitor 331 is in the normal state or the abnormal state, based on the comparison between the voltage value applied to the PTC thermistor 332 and the voltage threshold. Accordingly, the voltage value applied to the PTC thermistor 332 when the control unit 340 detects that the microphone capacitor 331 is in the normal state is different from the voltage value applied to the PTC thermistor 332 when the control unit 340 detects that the microphone capacitor 331 is in the abnormal state.

When the control unit 340 detects that the microphone capacitor 331 is in the normal state (ST103: NO), the process in step ST103 is performed again. That is, when the aerosol inhaler 1 is in the active state, the process of detecting whether the microphone capacitor 331 is in the abnormal state is always performed. Such a configuration enables the control unit 340 to detect all the troubles that have occurred in the microphone capacitor 331.

When detecting that the microphone capacitor 331 is in the abnormal state (ST103: YES), the control unit 340 causes the memory unit 350 to store the information on the abnormal state (ST104). Specifically, the control unit 340 causes the memory unit 350 to store the content of the trouble (the occurrence of the short circuit) that has occurred in the microphone capacitor 331. The content of the trouble is thus stored in the memory unit 350, thereby making it possible to easily recognize the content of the trouble without having to perform a special inspection when the aerosol generation device 1 is repaired at a later date. Accordingly, the man-hours required for repair can be significantly reduced.

The control unit 340 operates the notification unit 360 (ST105). Specifically, the control unit 340 causes the notification unit 360 to emit light. This makes it possible to notify the user who is using the aerosol generation device 1 that the microphone capacitor 331 has a trouble.

The control unit 340 causes the aerosol generation device 1 to undergo the transition from the active state to the sleep state (ST106). That is, in the case where the trouble has occurred in the microphone sensor 331, the aerosol suction device 1 thus undergoes the transition to the sleep state in which the aerosol is not generated, so that the electric power can be prevented from being supplied to each portion of the aerosol generation device 1, even if the aerosol cannot be normally generated. That is, the waste of the electric power can be prevented.

As described above, in the aerosol generation device 1 in the present embodiment, the control unit 340 compares the voltage value applied to the microphone capacitor 331 with the preset voltage threshold equal to or higher than the point B, and detects whether the microphone capacitor 331 is in the normal state or the abnormal state. Specifically, when the voltage value applied to the PTC thermistor 332 is equal to or higher than the voltage threshold, the control unit 340 detects that the microphone capacitor 331 is in the abnormal state. Accordingly, the aerosol generation device 1 in the present embodiment can detect the occurrence of a trouble in the sensor that detects the user's suction action.

In the aerosol generation device 1 in the present embodiment, the PTC thermistor 332 having the overcurrent protection function is adopted as a configuration for detecting the trouble in the microphone capacitor 331. Such a configuration makes it possible to prevent secondary damages in which the overcurrent due to a trouble in the microphone capacitor 331 flows in the aerosol generation device 1 and a trouble occurs in a configuration other than the sensor unit 330 of the aerosol generation device 1. That is, such a configuration makes it possible to achieve objects to detect the trouble in the sensor and prevent the trouble in the other configuration due to the trouble in the sensor.

According to the present embodiment, in the case where a trouble has occurred in the sensor, such a trouble can be detected, thereby making it possible to prevent the aerosol source from being atomized by the aerosol generation device and being wasted, when the user does not perform the suction action, for example. That is, the aerosol generation device in the present embodiment can achieve the effects of resource saving and energy saving.

In the above-described embodiment, the state detection process to be performed by the control unit 340 has been described by the example illustrated in FIG. 6, but is not limited thereto. For example, the state detection process to be performed by the control unit 340 may be as in the example illustrated in FIG. 7.

A flowchart illustrated in FIG. 7 is different from the flowchart illustrated in FIG. 6 in that ST201 to ST203 are added, and the process of ST101 is performed again after the process of ST106. Note that ST203 is a process in which the control unit 340 causes the memory unit 350 to store the number of times that the control unit 340 has detected that the microphone capacitor 331 is in the abnormal state (the number of times of detection).

Hereafter, the flowchart illustrated in FIG. 7 will be described, mainly focusing on the above-described differences, assuming that the process of ST203 is already performed a plurality of times, that is, the control unit 340 detects, a plurality of times, that the microphone capacitor 331 is in the abnormal state.

In the flowchart illustrated in FIG. 7, when the control unit 340 detects that the microphone capacitor 331 is in the abnormal state (ST103: YES), the process of ST101 is performed again after the processes of ST104, ST203, ST105, and ST106. Accordingly, in the flowchart illustrated in FIG. 7, the process of ST203 may be performed a plurality of times. Therefore, the number of times of detecting that the microphone capacitor 331 is in the abnormal state, which is stored in the memory unit 340, may be updated.

When the power supply button 310 is pressed again in ST 101 (ST101: YES), the control unit 340 reads the information stored in the memory unit 350 (ST201). Specifically, the control unit 340 reads the number of times of detection and the limit threshold which is a threshold limiting the state transition of the aerosol generation device 1 from the sleep state to the active state.

Then, the control unit 340 determines whether the number of times of detection is less than the limit threshold (ST202). When the number of times of detection is less than the limit threshold (ST202: YES), the processes of ST102 and the subsequent steps are performed. For example, when the number of times of detection is 2 and the limit threshold is 3, the processes of ST102 and the subsequent steps are performed.

On the other hand, when the number of times of detection is equal to or greater than the limit threshold (ST202: NO), the process ends. For example, when the number of times of detection is 3 and the limit threshold is 3, the process ends. That is, the aerosol generation device 1 does not undergo the transition from the sleep state to the active state even when the power supply button 310 is pressed afterwards. The following is the reason why the state transition of the aerosol generation device 1 is controlled based on the comparison between the number of times of detection and the limit threshold.

When being wet with the aerosol source that has leaked out from the storage unit 110, the microphone capacitor 331 may temporarily malfunction. Specifically, the diaphragm 331A in the microphone capacitor 331 does not normally vibrate due to being wet with the aerosol source, which may cause the malfunction of the microphone capacitor 331. Then, the control unit 340 may detect, based on such malfunction, that the microphone capacitor 331 is in the abnormal state. When the wetting with the aerosol source is eliminated by drying or the like, the diaphragm 331A is often returned to a normal vibration state. That is, the malfunction due to the wetting with the aerosol source can be often eliminated when the wetting is dried.

Based on such a fact, when the number of detection times is less than the limit threshold, the abnormal state of the microphone capacitor 331 is considered to be caused by temporary malfunction due to the wetting with the aerosol source. In this case, when the power supply button 310 is pressed, the aerosol generation device 1 is configured to undergo the transition to the active state again.

On the other hand, when the number of times of detection reaches the limit threshold or more, the abnormal state of the microphone capacitor 331 is considered to be caused by a permanent trouble such as a short circuit. In this case, the aerosol generation device 1 does not undergo the transition again from the sleep state to the active state.

Accordingly, in the flowchart of the detection process illustrated in FIG. 7, a determination is made whether the abnormal state of the microphone capacitor 331 is temporarily caused by the leakage of the aerosol source or is permanently caused by a short circuit or the like, and the state transition of the aerosol generation device 1 is controlled based on such a determination. Accordingly, this can prevent a condition where the aerosol generation device 1 cannot be used even though the aerosol generation device 1 does not have a permanent trouble, whereby the convenience in using the aerosol generation device 1 can be improved.

Figure 8:
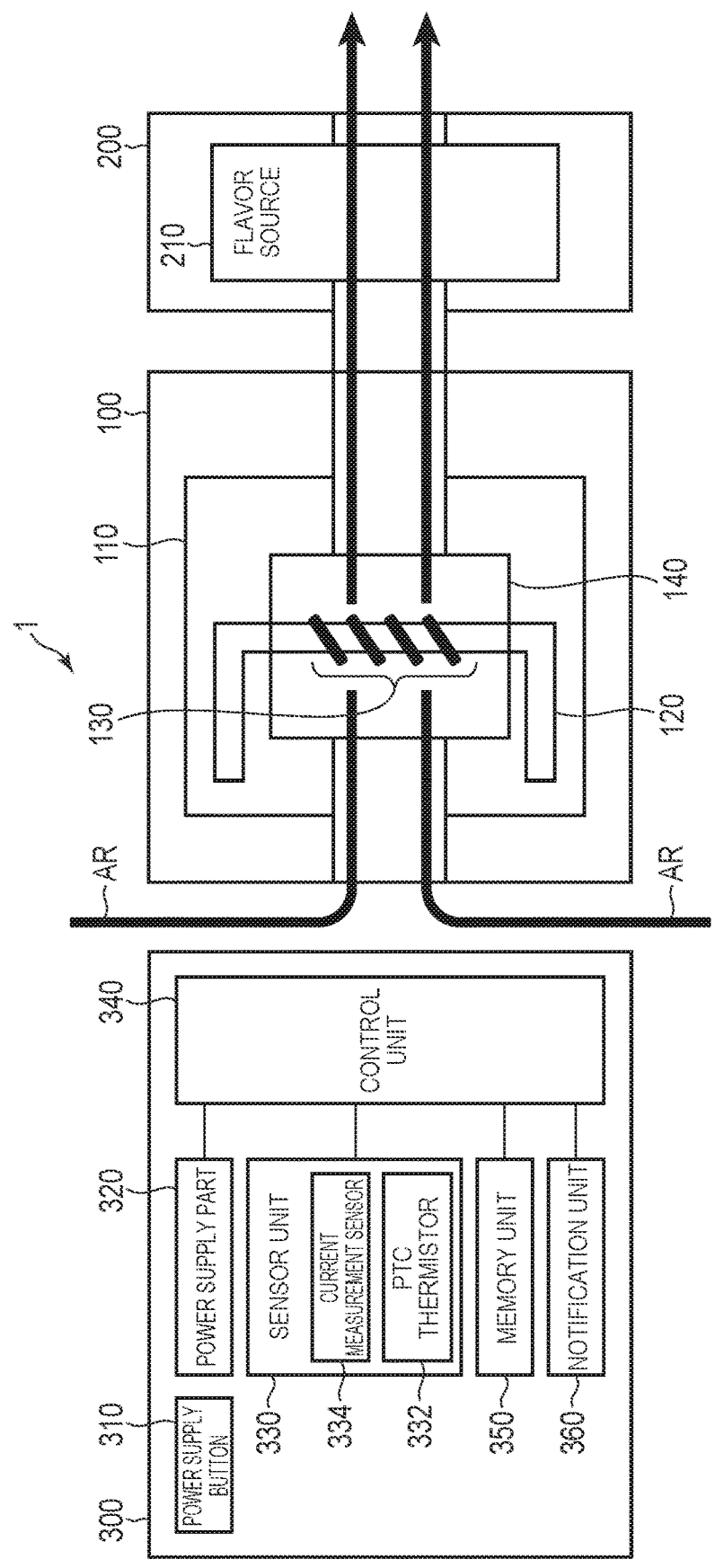
FIG. 8 is a block diagram illustrating an example of a schematic configuration of an aerosol generation device according to a modified example of the first embodiment of the present invention.

In the above-described embodiment, an example in which the PTC thermistor 332 is used as the second sensor has been described, but the second sensor is not limited to the PTC thermistor 332. For example, as the second sensor, a current measurement sensor 334 that measures a current may be used. FIG. 8 is a block diagram illustrating an example of a schematic configuration of an aerosol generation device 1 when the current measurement sensor 334 is adopted instead of the PTC thermistor 332. The same constituent elements as the constituent elements in FIG. 1 are denoted by the same reference signs.

In the case where a power supply unit 300 of the aerosol generation device 1 is configured as illustrated in FIG. 8, a value output from the current measurement sensor 334 to a control unit 340 is a value of a current flowing in the current measurement sensor 334, the current changing according to an electrical change in the microphone capacitor 331. Then, the control unit 340 detects, based on the current value, whether the microphone capacitor 331 is in the normal state or the abnormal state. Specifically, the control unit 340 compares the current value with a predetermined current threshold, and when the current value is equal to or greater than the current threshold, the control unit 340 detects that the microphone capacitor 331 has a trouble (a short circuit) such as a short circuit.

In the present embodiment, the description has been made assuming that the aerosol generation device 1 generates the aerosol in response to the user's suction action, but the configuration of the aerosol generation device 1 is not limited thereto. For example, the aerosol generation device 1 may be configured to generate invisible vapor in response to the user's suction action. Even in such a configuration, the same effects as those of the above-described embodiment can be obtained.

In the present embodiment, the description has been made assuming that the notification unit 360 emits the light according to the control by the control unit 340, but the configuration of the notification unit 360 is not limited thereto. For example, the notification unit 360 may be configured to vibrate in a predetermined vibration pattern or output a predetermined sound when the control unit 340 detects that the microphone capacitor 331 is in the abnormal state. Alternatively, the notification unit 360 may make a notification by combining them. Specifically, for example, the notification unit 360 may make a notification with a combination of light and vibration, or may make a notification with a combination of light, vibration, and sound.

Second Embodiment

Hereinafter, an aerosol generation device according to the present embodiment will be described. The aerosol generation device according to the present embodiment is, for example, an inhaler with which a user inhales the generated aerosol. The inhaler may be a heating type cigarette or an electronic cigarette. However, the inhaler is not limited thereto, and may be, for example, an inhaler for inhaling a drug. Note that the inhaler may generate invisible vapor instead of the aerosol.

Figure 9:
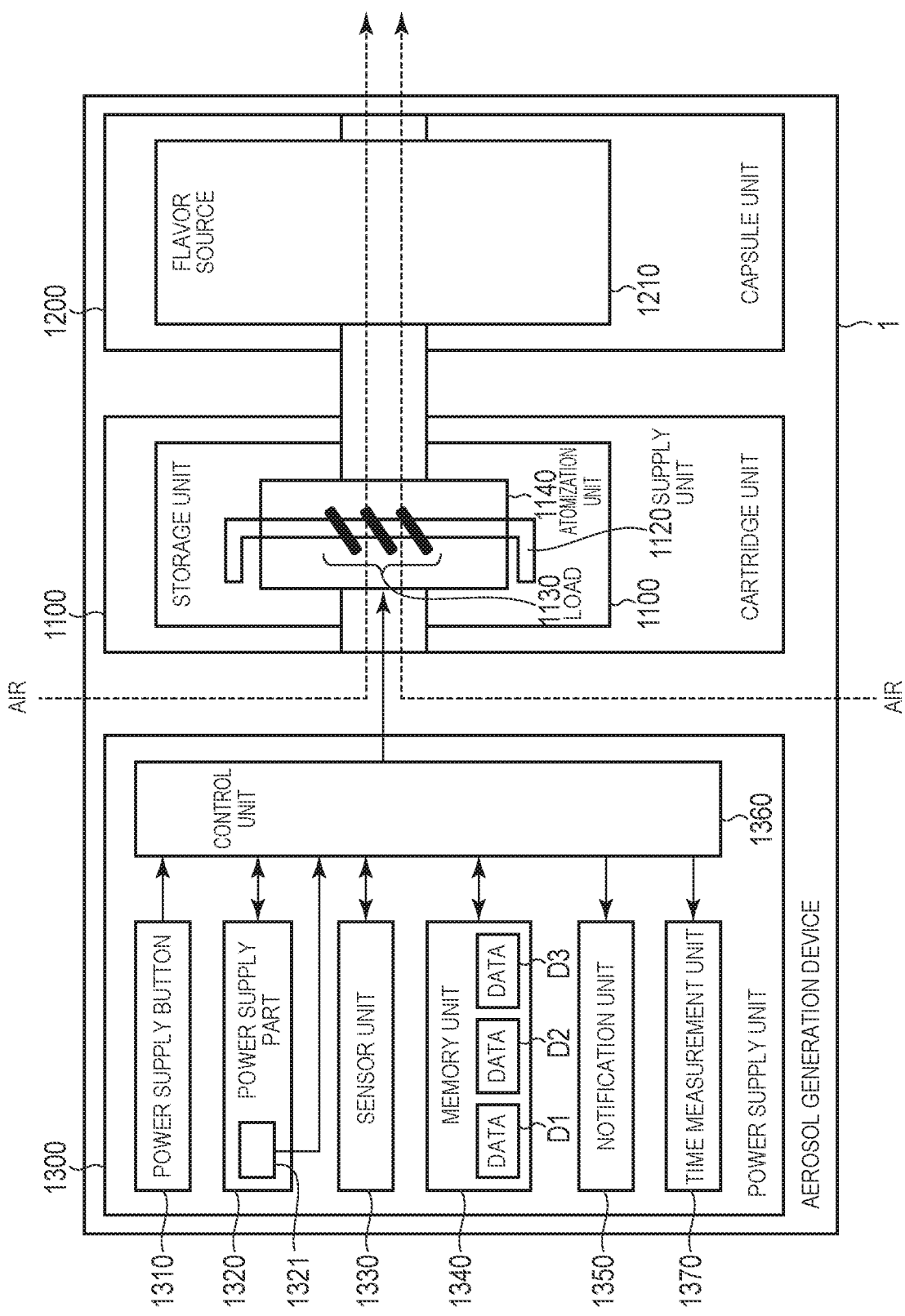
FIG. 9 is a block diagram illustrating an example of a configuration of an aerosol generation device according to a second embodiment of the present invention.

FIG. 9 is a block diagram illustrating an example of a configuration of an aerosol generation device 1000 according to the present embodiment. As illustrated in FIG. 1, the aerosol generation device 1000 includes a cartridge unit 1100, a capsule unit 1200, and a power supply unit 1300.

The aerosol generation device 1000 may be formed, for example, in a substantially cylindrical shape, so that a user can easily hold the aerosol generation device 1000. Note that the cartridge unit 1100, the capsule unit 1200, and the power supply unit 1300 may be configured to be connected to one another in a non-detachable or detachable manner.

The configuration of the cartridge unit 1100 is similar to the configuration of the cartridge unit 100 illustrated in FIG. 1, and accordingly the repeated description is not made here.

The configuration of the capsule unit 1200 is similar to the configuration of the capsule unit 200 illustrated in FIG. 1, and accordingly the repeated description is not made here.

As illustrated in FIG. 9, the power supply unit 1300 includes a power supply button 1310, a power supply part 1320, a sensor unit 1330, a memory unit 1340, a notification unit 1350, a control unit 1360, and a time measurement unit 1370.

In the power supply unit 1300, there is generated an error signal different for each type of trouble that has occurred in the power supply part 1320. Examples of the trouble in the power supply part 1320 include the deterioration of the power supply part 1320 and/or the failure of the power supply.

The power supply button 1310 is a button for causing an operating state transition of the aerosol generation device 1000. When the power supply button 1310 is pressed to turn on the power supply, the aerosol generation device 1000 undergoes the transition to an active state, which will be described later. When the power supply button 1310 is pressed to turn off the power supply while the aerosol generation device 1000 is in the active state, the aerosol generation device 1000 undergoes the transition from the active state to a sleep state, which will be described later.

The power supply part 1320 is, for example, a rechargeable battery such as a lithium-ion secondary battery, and its type is not limited. The power supply part 1320 supplies the electric power to each portion of the aerosol generation device 1000 based on the control by the control unit 1360. In addition, the power supply part 1320 includes a temperature sensor 1321 such as a thermistor, for example. The temperature sensor 1321 is provided in a battery pack of the power supply part 1320, for example. The information indicating a temperature of the power supply part 1320 measured by the temperature sensor 1321 is stored in the memory unit 1340 by the control unit 1360. Note that the power supply part 1320 can be in a normal state in which there is no trouble or a trouble state in which a trouble has occurred.

The sensor unit 1330 is a sensor that outputs a predetermined output value (for example, a voltage value or a current value) to the control unit 1360 according to, for example, the flow rate and/or the flow velocity of gas passing through a position where the sensor unit 1330 is mounted. Such a sensor unit 1330 is used to detect a user's suction action (an action for requesting the aerosol generation device 1000 to generate the aerosol). Although various types of sensors can be used as the sensor unit 1330, for example, a microphone capacitor, a pressure sensor, or a fluid sensor is used.

The memory unit 1340 is, for example, a non-volatile memory. The memory unit 1340 stores data D1 including various types of information acquired by the control unit 1360. In addition, the memory unit 1340 stores data D2 including various types of information used for the control by the control unit 1360. Furthermore, the memory unit 1340 stores data D3 including various types of information generated by the control unit 1360.

Here, the data D1 stores the information including an operation value related to an operation of the power supply part 1320, for example. Specifically, the data D1 includes the information indicating a voltage value of the power supply part 1320, a total charging time period of the power supply part 1320, and a temperature of the power supply part 1320, for example. In addition, the data D2 includes the information indicating various predetermined thresholds, various predetermined voltage ranges, and a relationship between a content of a trouble that has occurred in the power supply part 1320 and an error signal corresponding to the content, for example. Furthermore, the data D3 includes trouble information indicating a content or cause of a trouble that has occurred in the power supply part 1320, for example.

When receiving an error signal generated by the control unit 1360 based on the data D2, the error signal corresponding to the trouble that has occurred in the power supply part 1320, the notification unit 1350 outputs, for example, light and/or sound according to the error signal. Note that the notification unit 1350 may vibrate according to the error signal received from the control unit 1360, for example. Specifically, the notification unit 1350 may be, for example, a light-emitting device such as an LED, a sound output device such as a speaker, or a vibration generating device.

In this way, the notification unit 1350 makes a notification in a different mode for each type of the error signal received from the control unit 1360. Such a configuration makes it possible to notify a user and/or the like of the aerosol generation device 1000 of the content or cause of the trouble that has occurred in the power supply part 1320. The modes of the notification made by the notification unit 1350 according to the trouble that has occurred in the power supply part 1320 are described below for illustrative purposes. For example, the notification unit 1350 may make a notification by freely combining, for example, light, sound, and vibration according to the content of the trouble.

When receiving, from the power supply button 1310, a notification that the power supply button 1310 has been pressed, the control unit 1360 causes the aerosol generation device 1000 to undergo the transition to one of two operating states. The two operating states include an active state (equivalent to a power supply on state) in which the electric power can be supplied from the power supply part 1320 to each portion of the aerosol generation device 1000 and a sleep state (equivalent to a power supply off state) in which no electric power can be supplied from the power supply part 1320 to each portion of the aerosol generation device 1000 or only minimal electric power can be supplied from the power supply part 1320 to each portion of the aerosol generation device 1000. When the sensor unit 1330 detects the user's suction action while the aerosol generation device 1000 is in the active state, the control unit 1360 causes the power supply part 1320 to supply the electric power to a load 1130 to atomize the aerosol source. When the power supply unit 1300 is in the sleep state, the control unit 1360 does not cause the power supply part 1320 to supply the electric power to the load 1130 even when the user performs a suction action. Therefore, the aerosol source is not atomized.

When acquiring an operation value related to an operation of the power supply part 1320, the control unit 1360 causes the memory unit 1340 to store the data D1 including the operation value. Here, the operation value includes the information indicating a voltage value of the power supply part 1320, a total charging time period of the power supply part 1320, and a temperature of the power supply part 1320, for example.

For example, while the power supply part 1320 is charged or discharged, the control unit 1360 reads the data D1 and the data D2 from the memory unit 1340, and determines whether the power supply part 1320 is in the normal state or the trouble state based on the operation value included in the data D1 and the various predetermined thresholds and/or various predetermined voltage ranges included in the data D2. Note that when determining that the power supply part 1320 is in the trouble state, the control unit 1360 identifies the content of cause of the trouble that has occurred in the power supply part 1320, and causes the memory unit 1340 to store the data D3 including the trouble information indicating the content or cause of the trouble.

In the present embodiment, the trouble state of the power supply part 1320 is subdivided for each content or cause of the trouble that has occurred in the power supply part 1320. Then, when detecting one among the plurality of states included in the trouble state, the control unit 1360 generates an error signal of a type corresponding to the detected state. Then, the control unit 1360 transmits the generated error signal to the notification unit 1350, and causes the notification unit 1350 to make a notification in a mode based on the error signal. In other words, the control unit 1360 causes the notification unit 1350 to make a notification in a different mode for each type of the error signal.

In the present embodiment, the control unit 1360 may causes the notification unit 1350 to make a notification based on the generated signal, for example, when detecting a trouble (for example, when generating an error signal), when causing the aerosol generation device 1000 to undergo the transition to the active state (for example, when receiving a signal indicating that the power supply button 1310 is pressed to turn on the power supply), when detecting suction start of the aerosol (for example, when receiving a generation request signal from the sensor unit 1330), when an aerosol suction action is performed (for example, when being able to determine that the suction action is continued, based on the output of the sensor unit 1330), when charging of the power supply part 1320 is started (for example, when detecting that a charging connector has been connected to the power supply unit 1300), or when the power supply part 1320 is charged (for example, a power supply voltage of the power supply part 1320 increases).

For example, as a first notification mode, the control unit 1360 causes the notification unit 1350 to emit light in a different mode for each type of the error signal. For example, when receiving the error signal, the notification unit 1350 may alternately emit the cold color light and the warm color light.

For example, as a second notification mode, the control unit 1360 causes the notification unit 1350 to generate vibration in a different mode for each type of the error signal.

For example, as a third notification mode, the control unit 1360 causes the notification unit 1350 to generate sound in a different mode for each type of the error signal.

When determining that the power supply part 1320 is in the trouble state, the control unit 1360 may inhibit the charging or discharging of the power supply part 1320. In addition, when determining that the power supply part 1320 is in the trouble state, the control unit 1360 may stop heating of the load 1130. Such a configuration makes it possible to prevent the progression of the trouble that has occurred in the power supply part 1320.

Hereinafter, the description will be made regarding a specific example of a process of determining whether the power supply part 1320 is in the trouble state (hereinafter, referred to as a "trouble detection process") by the control unit 1360. Note that, in the present embodiment, the description will be made assuming that the trouble state of the power supply part 1320 may include first to fifth trouble states.

First Example of Problem Detection Process

Figure 10:
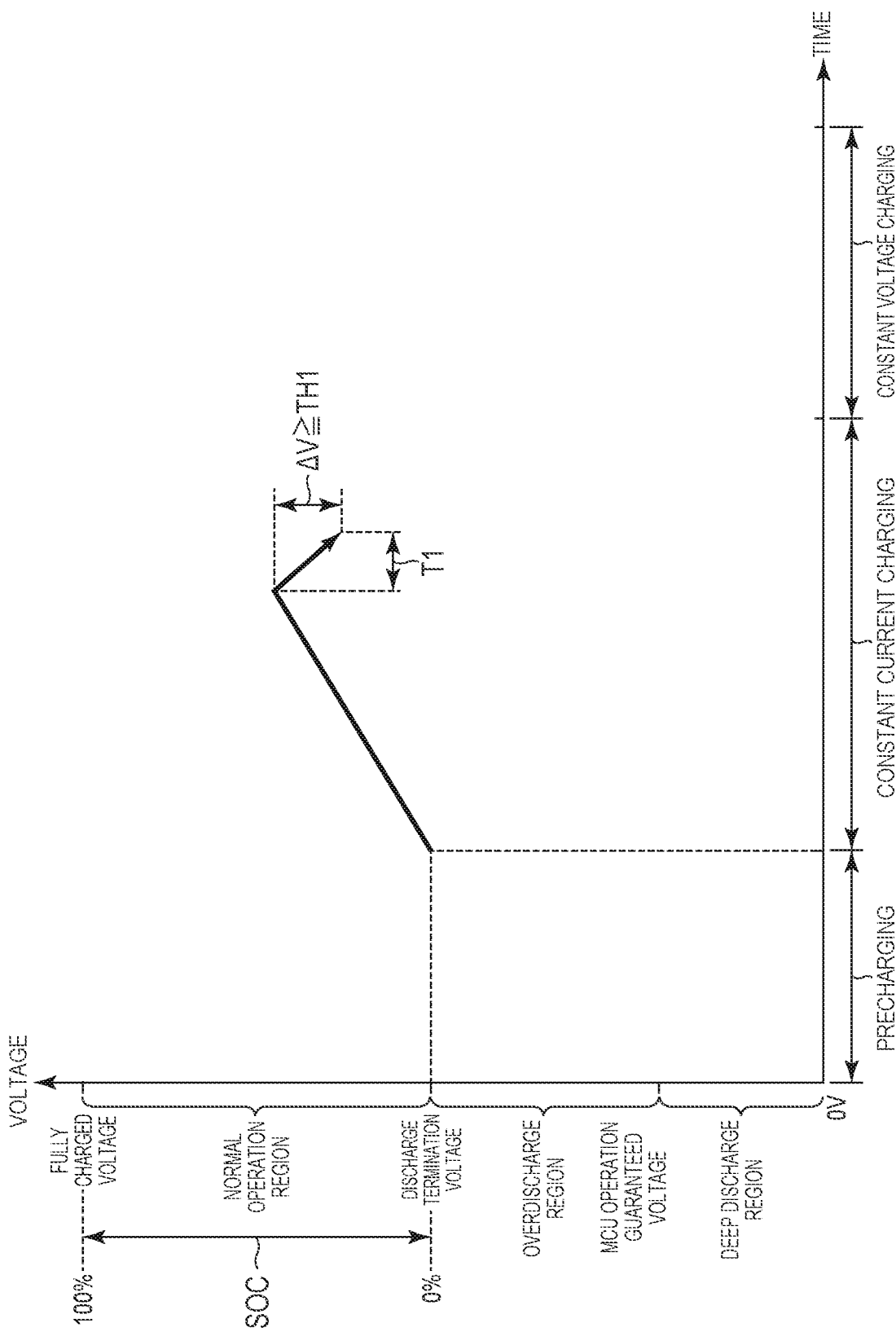
FIG. 10 is a graph showing a first example of a trouble detection process by a control unit according to the second embodiment of the present invention.

FIG. 10 is a graph showing a first example of a trouble detection process by the control unit 1360. The horizontal axis of the graph shown in FIG. 10 represents a time, and the vertical axis thereof represents a voltage of the power supply part 1320. In an example shown in FIG. 10, the control unit 1360 detects an internal short circuit which is one of the troubles in the power supply part 1320.

As shown in FIG. 10, a voltage region of the power supply part 1320 is divided into three regions: a normal operation region, an overdischarge region, and a deep discharge region, based on the voltage value of the power supply part 1320. Here, the normal operation region refers to a voltage range from a discharge termination voltage (for example, 3.0 V) to a fully charged voltage (for example, 4.0 V). The overdischarge region refers to a voltage range from the discharge termination voltage to a micro controller unit (MCU: equivalent to the control unit 1360) operation guaranteed voltage. The deep discharge range refers to a voltage range from the MCU operation guaranteed voltage to zero voltage (a state in which the voltage value of the power supply part 1320 is 0 V). Here, a state of charge (SOC) shown in FIG. 10 represents a charge rate of the power supply part 1320, and becomes 0% at the discharge termination voltage and 100% at the fully charged voltage.

As shown in FIG. 10, the control unit 1360 performs one of precharging, constant current charging, and constant voltage charging to charge the power supply part 1320 based on the voltage value of the power supply part 1320 and the like. Here, the precharging refers to charging performed when the voltage region of the power supply part 1320 is the overdischarge region or the deep discharge region, for example. The constant current charging refers to charging performed at a constant current value in the region from the discharge termination voltage to the fully charged voltage (normal operation region), for example. The constant voltage charging refers to charging performed to maintain the voltage value of the power supply part 1320 at a predetermined voltage value, and is performed to maintain the voltage value of the power supply part 1320 at the fully charged voltage, for example.

Here, when the constant current charging is performed in the normal operation region while the power supply part 1320 has no trouble, the voltage value of the power supply part 1320 increases with the passage of the charging time.

In the first example of the trouble detection process, the trouble in the power supply part 1320 is detected utilizing such a characteristic. Specifically, the control unit 1360 detects the trouble in the power supply part based on a change in the voltage value during charging of the power supply part 1320. More specifically, when detecting that an amount of decrease $\Delta V$ per a predetermined time period T1 of the voltage value of the power supply part 1320 is equal to or greater than a first threshold TH1, that is, when the voltage drop has occurred even during the charging, the control unit 1360 determines that the power supply part 1320 is in a first trouble state. When determining that the power supply part 1320 is in the first trouble state, the control unit 1360 causes the memory unit 1340 to store, as the data D3, the first trouble information indicating the first trouble state.

The control unit 1360 calculates or checks the above-described amount of decrease $\Delta V$ per a predetermined time period T1 and the threshold TH1 based on the data D1 and data D2 stored in the memory unit 1340 and the output from the time measurement unit 1370. Note that the time measurement unit 1370 is a member that can measure the time, such as a stopwatch or a clock, for example. The time measurement unit 1370 may be incorporated in the control unit 1360, for example.

Second Example of Problem Detection Process

Figure 11:
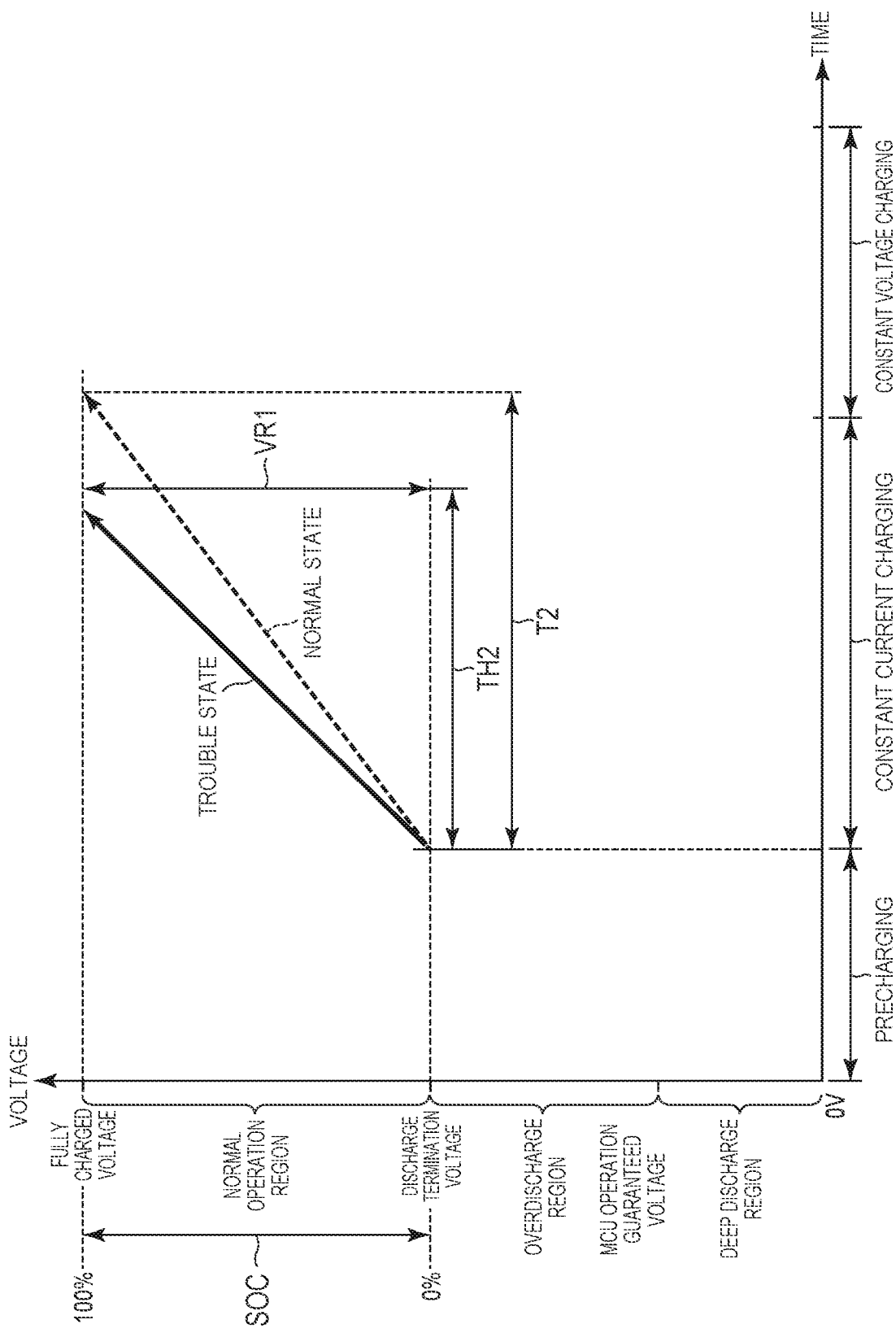
FIG. 11 is a graph showing a second example of a trouble detection process by the control unit according to the second embodiment of the present invention.

FIG. 11 is a graph showing a second example of a trouble detection process by the control unit 1360. In the graph shown in FIG. 11, common parts to those in the graph shown in FIG. 10 are not described. In the example shown in FIG. 11, the control unit 1360 detects the deterioration in the capacity which is one of the troubles in the power supply part 1320.

In the example shown in FIG. 11, a first voltage range VR1 included in the normal operation region is defined. That is, the first voltage range VR1 is defined by the voltage values from a lower limit (discharge terminal voltage) to an upper limit (fully charged voltage) of the normal operation region.

In the second example of the trouble detection process, the control unit 1360 detects the trouble in the power supply part 1320 based on a time period required for the voltage value of the power supply part 1320 to increase from the lower limit to the upper limit of the first voltage range VR1. Specifically, in the charging of the power supply part 1320, when detecting that a time period T2 required for the voltage value of the power supply part 1320 to increase from the lower limit to the upper limit of the first voltage range VR1 is equal to or less than a second threshold TH2, the control unit 1360 determines that the power supply part 1320 is in a second trouble state. Then, when determining that the power supply part 1320 is in the second trouble state, the control unit 1360 causes the memory unit 1340 to store, as the data D3, the second trouble information indicating the second trouble state.

The control unit 1360 calculates or checks the voltage value of the power supply part 1320, the first voltage range VR1, the time period T2, and the threshold TH2 described above based on the data D1 and data D2 stored in the memory unit 1340 and the output from the time measurement unit 1370.

Third Example of Problem Detection Process

Figure 12:
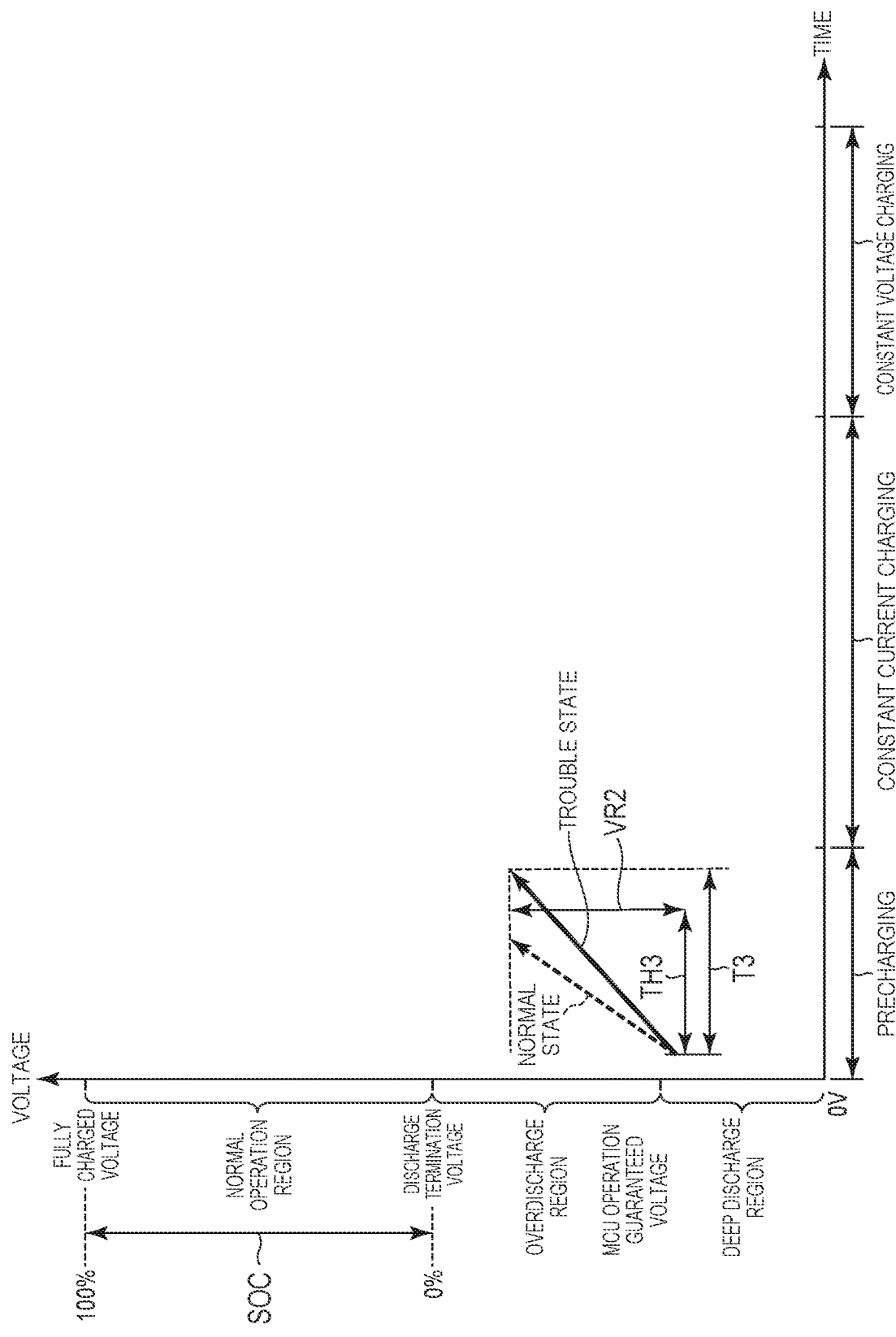
FIG. 12 is a graph showing a third example of a trouble detection process by the control unit according to the second embodiment of the present invention.

FIG. 12 is a graph showing a third example of a trouble detection process by the control unit 1360. In the graph shown in FIG. 12, common parts to those in the graph shown in FIG. 10 are not described. In the example shown in FIG. 12, the control unit 1360 detects the deterioration due to the overdischarge which is one of the troubles in the power supply part 1320.

In the example shown in FIG. 12, a second voltage range VR2 included in the deep discharge region and/or the overdischarge region is defined.

In the third example of the trouble detection process, the control unit 1360 detects the trouble in the power supply part 1320 based on a time period required for the voltage value of the power supply part 1320 to increase from a lower limit to an upper limit of the second voltage range VR2. Specifically, in the case where the precharging is performed to charge the power supply part 1320, when detecting that a time period T3 required for the voltage value of the power supply part 1320 to increase from the lower limit to the upper limit of the second voltage range VR2 is equal to or greater than a third threshold TH3, the control unit 1360 determines that the power supply part 1320 is in a third trouble state. Then, when determining that the power supply part 1320 is in the third trouble state, the control unit 1360 causes the memory unit 1340 to store, as the data D3, the third trouble information indicating the third trouble state.

The control unit 1360 calculates or checks the voltage value of the power supply part 1320, the second voltage range VR2, the time period T3, and the threshold TH3 describe above based on the data D1 and data D2 stored in the memory unit 1340 and the output from the time measurement unit 1370.

Fourth Example of Problem Detection Process

Figure 13:
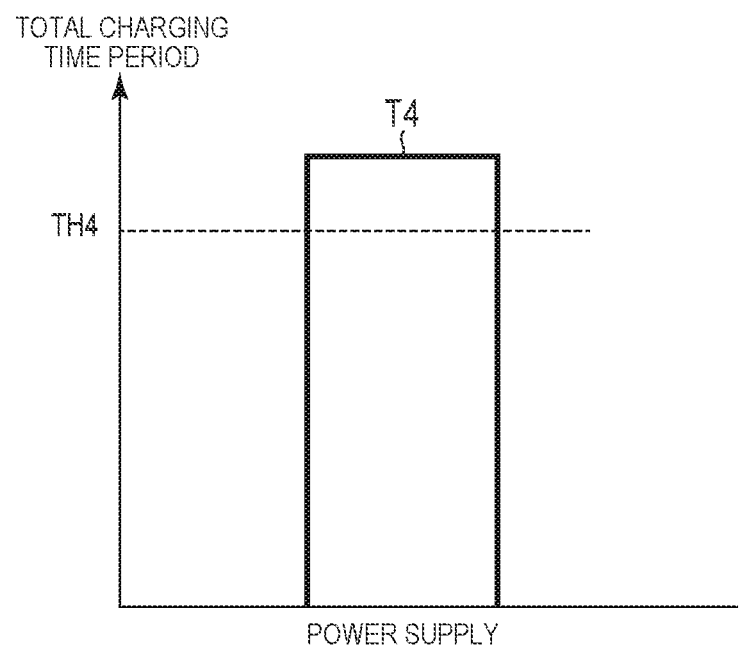
FIG. 13 is a graph showing a fourth example of a trouble detection process by the control unit according to the second embodiment of the present invention.

FIG. 13 is a graph showing a fourth example of a trouble detection process by the control unit 1360. The vertical axis of the graph shown in FIG. 13 represents a total charging time period T4 of the power supply part 1320. In an example shown in FIG. 13, the control unit 1360 detects a lifespan of the power supply part 1320 which is one of the troubles in the power supply part 1320.

The control unit 1360 counts the total charging time period T4 of the power supply part 1320 as an operation value of the power supply part 1320, and causes the memory unit 1340 to store, as the data D1, the counted total charging time period T4. When detecting that the total charging time period T4 of the power supply part 1320 indicated in the data D1 is equal to or greater than a fourth threshold TH4 indicated in the data D2, the control unit 1360 determines that the power supply part 1320 is in a fourth trouble state. Then, when determining that the power supply part 1320 is in the fourth trouble state, the control unit 1360 causes the memory unit 1340 to store fourth trouble information indicating the fourth trouble state.

Fifth Example of Problem Detection Process

Figure 14:
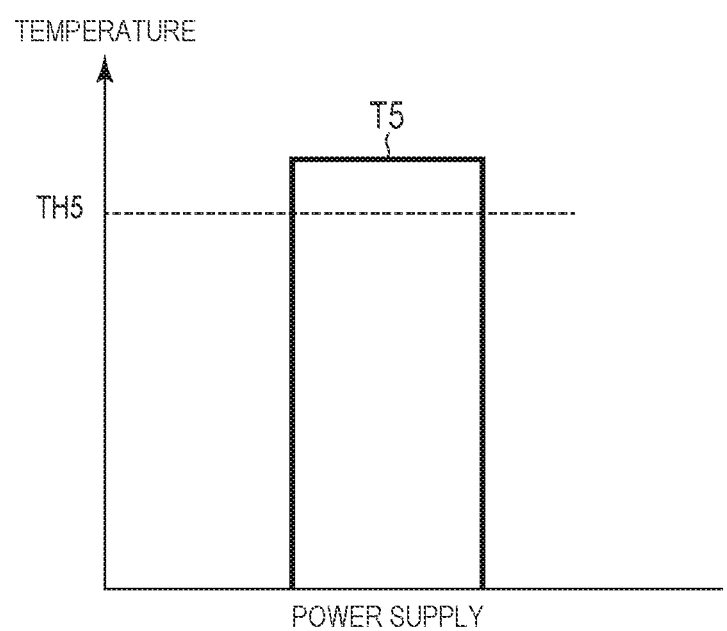
FIG. 14 is a graph showing a fifth example of a trouble detection process by the control unit according to the second embodiment of the present invention.

FIG. 14 is a graph showing a fifth example of a trouble detection process by the control unit 1360. The vertical axis of the graph shown in FIG. 14 represents a temperature of the power supply part 1320. In an example shown in FIG. 14, the control unit 1360 detects a temperature abnormality in the power supply part 1320 which is one of the troubles in the power supply part 1320.

The control unit 1360 acquires, as an operation value of the power supply part 1320, the information indicating a temperature T5 of the power supply part 1320 measured by the temperature sensor 1321 from the data D1 stored in the temperature sensor 1321 or the memory unit 1340. Then, when the temperature T5 of the power supply part 1320 is equal to or higher than a fifth threshold TH5 indicated in the data D2, the control unit 1360 determines that the power supply part 1320 is in a fifth trouble state. Then, when determining that the power supply part 1320 is in the fifth trouble state, the control unit 1360 causes the memory unit 1340 to store fifth trouble information indicating the fifth trouble state.

However, for example, the control unit 1360 may acquire the temperature T5 of the power supply part 1320 when the aerosol generation device 1000 undergoes the transition from the sleep state to the active state, may acquire the temperature T5 of the power supply part 1320 while the user's suction action is performed, may acquire the temperature T5 of the power supply part 1320 when the charging of the power supply part 1320 is started, or may acquire the temperature T5 of the power supply part 1320 while the power supply part 1320 is being charged, and the timing may be any timing.

Hereinafter, the description will be made regarding a specific example of a trouble notification process in which the control unit 1360 causes the notification unit 1350 to make a notification about a content or cause of the trouble that has occurred in the power supply part 1320.

Figure 15:
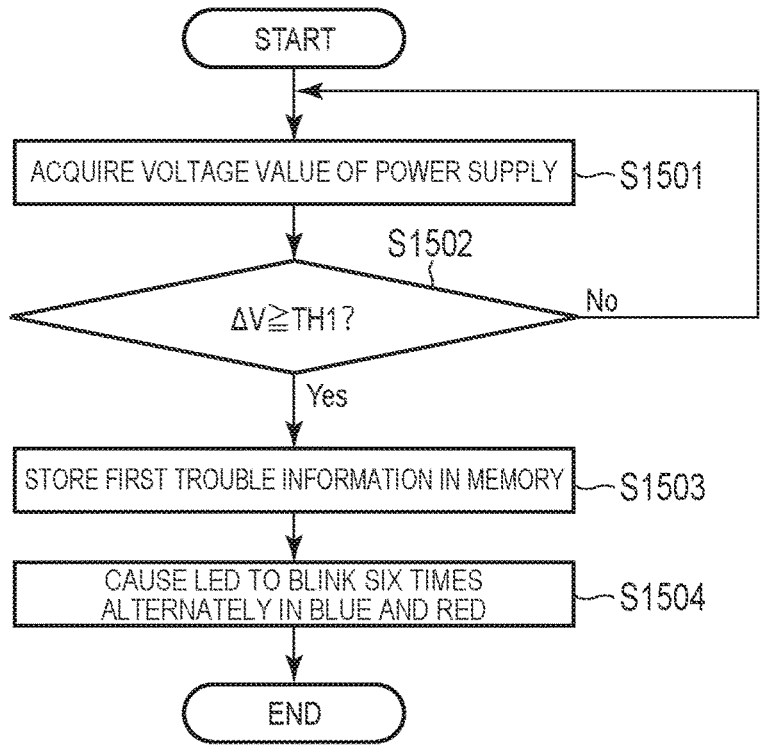
FIG. 15 is a flowchart illustrating the first example of the trouble detection process and an example of a trouble notification process related to such a trouble detection process.

FIG. 15 is an example of a flowchart illustrating the above-described first example of the trouble detection process and the trouble notification process related to such a trouble detection process.

In step S1501, when the power supply part 1320 is charged in the normal operation region, the control unit 1360 reads the data D1 stored in the memory unit 1320 and acquires the voltage value of the power supply part 1320.

In step S1502, when the power supply part 1320 is charged in the normal operation region, the control unit 1360 determines whether the amount of decrease ΔV per a predetermined time period T1 of the voltage value of the power supply part 1320 is equal to or greater than the first threshold TH1.

When the amount of decrease ΔV per a predetermined time period T1 is less than the first threshold TH1 (step S1502: No), the process returns to step $1501.

When the amount of decrease ΔV per a predetermined time period T1 is equal to or greater than the first threshold TH1 (step S1502: Yes), in step S1503, the control unit 1360 causes the memory unit 1340 to store, as the data D3, the first trouble information indicating that an internal short circuit has occurred in the power supply part 1320.

Then, in step S1504, the control unit 1360 transmits an error signal indicating the first trouble state to the notification unit 1350, and causes the notification unit 1350 to blink six times alternately in blue and red. That is, the control unit 1360 causes the notification unit 1350 to make a notification that the internal short circuit has occurred in the power supply part 1320. Then, the process ends. Note that, at the end of the process, the aerosol generation device 1000 has already undergone the transition to the sleep state.

Figure 16:
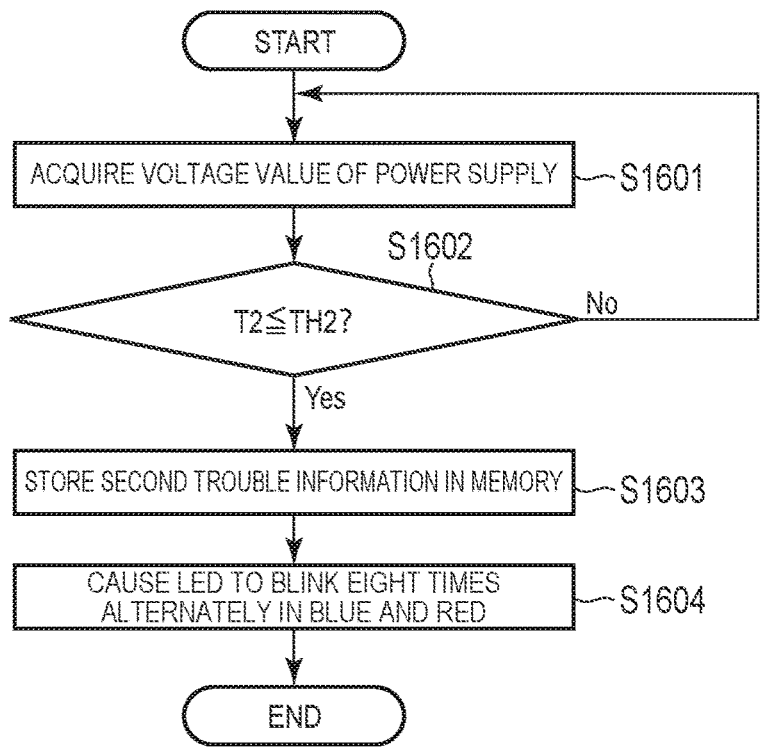
FIG. 16 is a flowchart illustrating the second example of the trouble detection process and an example of a trouble notification process related to such a trouble detection process.

FIG. 16 is an example of a flowchart illustrating the above-described second example of the trouble detection process and the trouble notification process related to such a trouble detection process.

In step S1601, when the power supply part 1320 is charged in the normal operation region, the control unit 1360 acquires the voltage value of the power supply part 1320.

In step S1602, when the power supply part 1320 is charged in the normal operation region, the control unit 1360 determines whether the time period T2 required for the voltage value of the power supply part 1320 to increase from the lower limit to the upper limit of the first voltage range VR1 is equal to or less than the second threshold TH2.

When the time period T2 exceeds the second threshold TH2 (step S1602: No), the process returns to step S1601.

When the time period T2 is equal to or less than the second threshold TH2 (step S1602: Yes), in step S1603, the control unit 1360 causes the memory unit 1340 to store, as the data D3, the second trouble information indicating that the capacity of the power supply part 1320 has deteriorated.

In step S1604, the control unit 1360 transmits an error signal indicating the second trouble state to the notification unit 1350, and causes the notification unit 1350 to blink eight times alternately in blue and red. That is, the control unit 1360 causes the notification unit 1350 to make a notification that the capacity of the power supply part 1320 has deteriorated. Then, the process ends. Note that, at the end of the process, the aerosol generation device 1000 has already undergone the transition to the sleep state.

Figure 17:
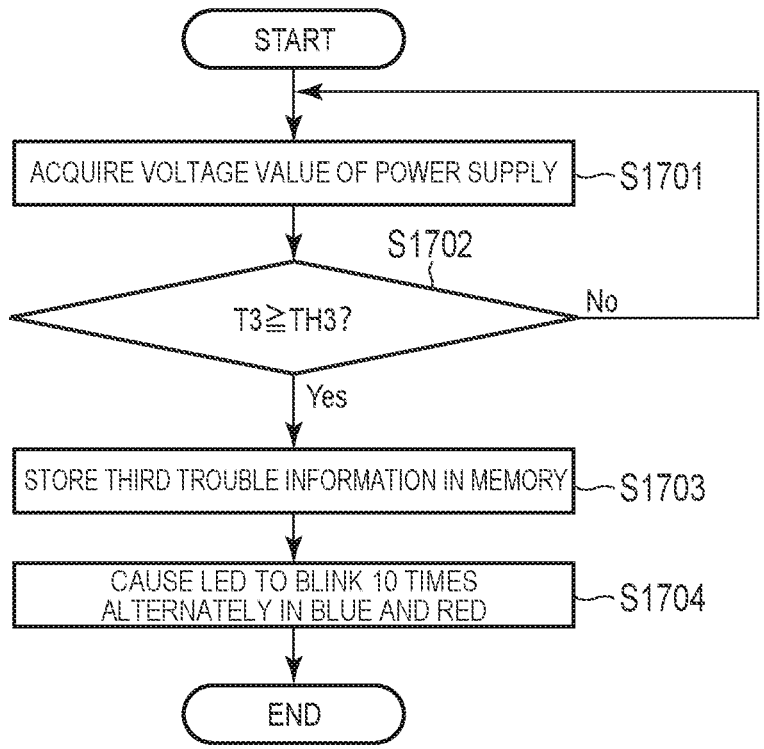
FIG. 17 is a flowchart illustrating the third example of the trouble detection process and an example of a trouble notification process related to such a trouble detection process.

FIG. 17 is an example of a flowchart illustrating the above-described third example of the trouble detection process and the trouble notification process related to such a trouble detection process.

In step S1701, when the power supply part 1320 is precharged in the deep discharge region and/or the overdischarge region, the control unit 1360 acquires the voltage value of the power supply part 1320.

In step S1702, when the power supply part 1320 is precharged in the deep discharge region and/or the overdischarge region, the control unit 1360 determines whether the time period T3 required for the voltage value of the power supply part 1320 to increase from the lower limit to the upper limit of the second voltage range VR2 is equal to or greater than the third threshold TH3.

When the time period T3 is less than the third threshold TH3 (step S1702: No), the process returns to step S1701.

When the time period T3 is equal to or greater than the third threshold TH3 (step S1702: Yes), in step S1703, the control unit 1360 causes the memory unit 1340 to store, as the data D3, the third trouble information indicating that the deterioration due to the overdischarge has occurred in the power supply part 1320.

In step S1704, the control unit 1360 transmits an error signal indicating the third trouble state to the notification unit 1350, and causes the notification unit 1350 to blink 10 times alternately in blue and red. That is, the control unit 1360 causes the notification unit 1350 to make a notification that the deterioration due to the overdischarge has occurred in the power supply part 1320. Then, the process ends. Note that, at the end of the process, the aerosol generation device 1000 has already undergone the transition to the sleep state.

Figure 18:
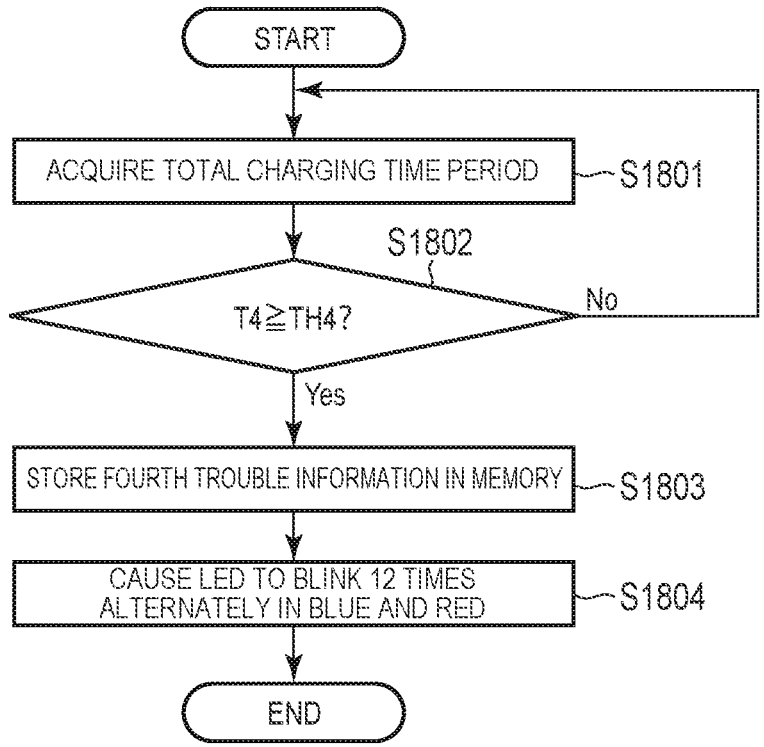
FIG. 18 is a flowchart illustrating the fourth example of the trouble detection process and an example of a trouble notification process related to such a trouble detection process.

FIG. 18 is an example of a flowchart illustrating the above-described fourth example of the trouble detection process and the trouble notification process related to such a trouble detection process.

In step S1801, the control unit 1360 acquires the total charging time period T4 of the power supply part 1320. For example, the control unit 1360 reads the data D1 stored in the memory unit 1340 and acquires the total charging time period T4.

In step S1802, the control unit 1360 determines whether the total charging time period T4 of the power supply part 1320 is equal to or greater than the fourth threshold TH4.

When the total charging time period T4 is less than the fourth threshold TH4 (step S1802: No), the process returns to step S1801.

When the total charging time period T4 is equal to or greater than the fourth threshold TH4 (step S1802: Yes), in step S1803, the control unit 1360 causes the memory unit 1340 to store, as the data D3, the fourth trouble information indicating that the power supply part 1320 has reached the end of lifespan.

In step S1804, the control unit 1360 transmits an error signal indicating the fourth trouble state to the notification unit 1350, and causes the notification unit 1350 to blink 12 times alternately in blue and red. That is, the control unit 1360 causes the notification unit 1350 to make a notification that the power supply part 1320 has reached the end of lifespan. Then, the process ends. Note that, at the end of the process, the aerosol generation device 1000 has already undergone the transition to the sleep state.

Figure 19:
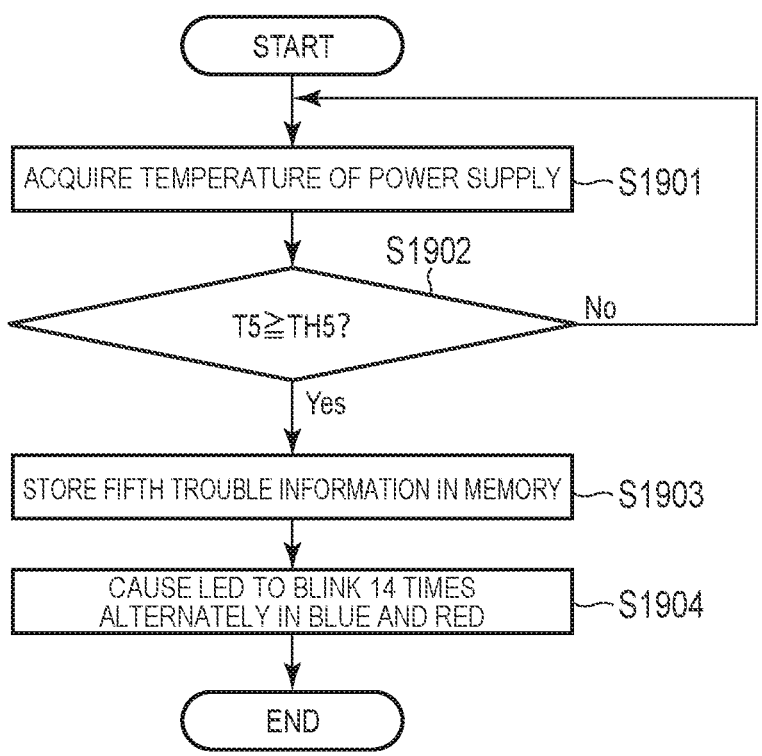
FIG. 19 is a flowchart illustrating the fifth example of the trouble detection process and an example of a trouble notification process related to such a trouble detection process.

FIG. 19 is an example of a flowchart illustrating the above-described fifth example of the trouble detection process and the trouble notification process related to such a trouble detection process.

In step S1901, the control unit 1360 acquires the temperature T5 of the power supply part 1320 from the data D1 stored in the temperature sensor 1321 or the memory unit 1340.

In step S1902, the control unit 1360 determines whether the temperature T5 is equal to or higher than the fifth threshold TH5.

When the temperature T5 is lower than the fifth threshold TH5 (step S1902: No), the process returns to step S1901.

When the temperature T5 is equal to or higher than the fifth threshold TH5 (step S1902: Yes), in step S1903, the control unit 1360 causes the memory unit 1340 to store, as the data D3, the fifth trouble information indicating that the temperature abnormality has occurred in the power supply part 1320.

In step S1904, the control unit 1360 transmits an error signal indicating the fifth trouble state to the notification unit 1350, and causes the notification unit 1350 to blink 14 times alternately in blue and red. That is, the control unit 1360 causes the notification unit 1350 to make a notification that the temperature abnormality has occurred in the power supply part 1320. Then, the process ends. Note that, at the end of the process, the aerosol generation device 1000 has already undergone the transition to the sleep state.

FIG. 20 is a flowchart illustrating an example of a notification process of first to fifth trouble states while the user's suction action is performed. Note that the description is made assuming that the processing illustrated in FIG. 20 is performed after the processing illustrated in FIGS. 15 to 19, but is not limited thereto.

In step S2001, the control unit 1360 determines whether the power supply button 1310 has been pressed so that the aerosol generation device 1000 has undergone the transition from the sleep state to the active state.

When the power supply button 1310 is not pressed (step S2001: No), that is, when the aerosol generation device 1000 does not undergo the transition from the sleep state to the active state, the process returns to step S2001, and therefore the notification process does not proceed.

When the power supply button 1310 has been pressed (step S2001: Yes), that is, when the aerosol generation device 1000 has undergone the transition from the sleep mode to the active mode, in step S2002, the control unit 1360 determines whether the trouble information (specifically, at least one of the first to fifth trouble information) is stored as the data D3 in the memory unit 1340.

When the trouble information is not stored in the memory unit 1340 (step S2002: No), the notification process ends, and the control unit 1360 controls to normally generate the aerosol.

When the trouble information is stored in the memory unit 1340 (step S2002: Yes), in step S2003, the control unit 1360 determines whether (for example, the start of) the suction action has been detected by the sensor unit 1330.

When the suction is not detected (step S2003: No), the process returns to step S2003.

When the suction has been detected (step S2003: Yes), in step S2004, the control unit 1360 determines whether the first trouble information is stored as the data D3 in the memory unit 1340.

When the first trouble information is stored in the memory unit 1340 (step S2004: Yes), in step S2005, the control unit 1360 transmits, to the notification unit 1350, the error signal indicating the first trouble state, and causes the notification unit 1350 to blink six times alternately in blue and red. That is, the control unit 1360 causes the notification unit 1350 to make a notification that the internal short circuit has occurred in the power supply part 1320. Then, the process ends.

When the first trouble information is not stored in the memory unit 1340 (step S2004: No), in step S2006, the control unit 1360 determines whether the second trouble information is stored as the data D3 in the memory unit 1340.

When the second trouble information is stored in the memory unit 1340 (step S2006: Yes), in step S2007, the control unit 1360 transmits, to the notification unit 1350, the error signal indicating the second trouble state, and causes the notification unit 1350 to blink eight times alternately in blue and red. That is, the control unit 1360 causes the notification unit 1350 to make a notification that the capacity of the power supply part 1320 has deteriorated. Then, the process ends.

When the second trouble information is not stored in the memory unit 1340 (step S2006: No), in step S2008, the control unit 1360 determines whether the third trouble information is stored as the data D3 in the memory unit 1340.

When the third trouble information is stored in the memory unit 1340 (step S2008: Yes), in step S2009, the control unit 1360 transmits, to the notification unit 1350, the error signal indicating the third trouble state, and causes the notification unit 1350 to blink 10 times alternately in blue and red. That is, the control unit 1360 causes the notification unit 1350 to make a notification that the deterioration due to the overdischarge has occurred in the power supply part 1320. Then, the process ends.

When the third trouble information is not stored in the memory unit 1340 (step S2008: No), in step S2010, the control unit 1360 determines whether the fourth trouble information is stored as the data D3 in the memory unit 1340.

When the fourth trouble information is stored in the memory unit 1340 (step S2010: Yes), in step S2011, the control unit 1360 transmits, to the notification unit 1350, the error signal indicating the fourth trouble state, and causes the notification unit 1350 to blink 12 times alternately in blue and red. That is, the control unit 1360 causes the notification unit 1350 to make a notification that the power supply part 1320 has reached the end of lifespan. Then, the process ends.

When the fourth trouble information is not stored in the memory unit 1340 (step S2010: No), in step S2012, the control unit 1360 determines whether the fifth trouble state is stored in the memory unit 1340, transmits, to the notification unit 1350, the error signal indicating the fifth trouble state, and causes the notification unit 1350 to blink 14 times alternately in blue and red. That is, the control unit 1360 causes the notification unit 1350 to make a notification that the temperature abnormality has occurred in the power supply part 1320. Then, the process ends.

As described above, for example, the control unit 1360 according to the present embodiment makes the determination as to the trouble in the power supply part 1320 based on the voltage drop during the charging, the determination as to the trouble in the power supply part 1320 based on the charging rate, the determination as to the trouble in the power supply part 1320 based on the total charging time period, and the determination as to the trouble in the power supply part 1320 based on the temperature of the power supply part 1320. Then, when detecting, based on such determinations, that the trouble has occurred in the power supply part 1320, the control unit 1360 generates an error signal different for each content of cause of the trouble. Then, the control unit 1360 causes the notification unit 1350 to make a notification in a mode based on the error signal. This makes it possible for a user and/or a repair person and the like to easily understand the content or cause of the trouble that has occurred in the power supply part 1320 based on the mode of the notification by the notification unit 1350, whereby the user and/or the repair person and the like can properly address the trouble with understanding of the cause of the trouble that has occurred in the power supply part 1320.

In the present embodiment, the user and/or the repair person and the like can easily recognize the content or cause of the trouble in the power supply part 1320. Accordingly, it is unnecessary to separately perform an electrical inspection to identify what trouble has occurred in the aerosol generation device 1000 according to the present embodiment. Accordingly, in the present embodiment, the waste of the electric power can be prevented, and the energy-saving effect can be obtained.

In the present embodiment, when detecting the trouble state of the power supply part 1320, the control unit 1360 causes the notification unit 1350 to make a notification about the trouble state at a plurality of timings. Among the plurality of timings, the first timing may be when the trouble state is detected, and the second timing may be after the trouble state is detected. Here, the number of elements in the power supply unit 1300 to which the electric power is to be supplied from the power supply part 1320 at the first timing may be greater than the number of elements in the power supply unit 1300 to which the electric power is to be supplied from the power supply part 1320 at the second timing. Alternatively, the second timing may be a timing of detecting an instruction to cause the aerosol generation device 1000 to undergo the transition to the power supply on state, or may be a timing of detecting an aerosol generation request.

A timing of making a notification about the trouble state will be specifically described. When the trouble occurs in the power supply part 1320, the control unit 1360 according to the present embodiment causes the notification unit 1350 to make a notification corresponding to the type of the trouble at the timing of detecting the occurrence of the trouble and at the timing when the sensor unit 1330 detects a user's suction action after the occurrence of the trouble is detected. However, the timing of making a notification about the trouble is not limited thereto. For example, the control unit 1360 may cause the notification unit 1350 to make a notification corresponding to the type of the trouble at the timing of detecting the occurrence of the trouble and at the timing of detecting that the power supply button 1310 has been pressed after the above-described detection timing. Furthermore, the control unit 1360 may make a notification corresponding to the type of the trouble without supplying the electric power to each portion of the aerosol generation device 1000 such as the sensor unit 1330 (without causing the aerosol generation device 1000 to the transition from the sleep state to the active state). In this case, for example, even when the power supply part 1320 cannot supply sufficient electric power to the sensor 1330 and the like due to the trouble that has occurred, that is, even when it is difficult for the control unit 1360 to cause the notification unit 1350 to make a second notification (at the timing equivalent to the second timing) corresponding to the type of the trouble while the power supply part 1320 supplies the electric power to each portion, the second notification corresponding to the type of the trouble can be issued to the user and/or the like. In other words, the control unit 1360 can control so that the power consumption required for the second notification corresponding to the type of the trouble is smaller than the power consumption required for the first notification (at the timing equivalent to the first timing) (can reduce the number of elements in the power supply unit 1300 to which the electric power is supplied). This makes it possible to increase the opportunities to notify the user and/or the like of the occurrence of a trouble in the power supply part 1320 and the content or type of the trouble. Furthermore, a load to be applied to the power supply part 1320 that has a trouble can be reduced. Additionally, since the number of elements of the aerosol generation device 1000 to which the electric power is supplied at the above-described timing of detecting the occurrence of the trouble is greater than the number of elements of the aerosol generation device 1000 to which the electric power is supplied at the timing of detecting that the power supply button 1310 has been pressed after the above-described detection timing, the same effect can be achieved even when such timings of making a notification about the trouble are adopted.

In the present embodiment, a notification about a trouble may be made at various timings such as the timing of detecting the trouble, the timing of detecting the user's suction action, or the timing of causing the aerosol generation device 1000 to undergo the transition to the active state, for example. When the notification about the trouble is made at the timing of detecting the user's suction action or the timing of causing the aerosol generation device 1000 to undergo the transition to the active state, the user can easily recognize that the power supply part 1320 has a trouble when the user uses or starts using the aerosol generation device 1000.

In the present embodiment, notification modes corresponding to the types of the trouble states, respectively, can be freely changed, the notification modes being illustrated in step S1504 in FIG. 15, step S1604 in FIG. 16, step S1704 in FIG. 17, step S1804 in FIG. 18, step S1904 in FIG. 19, and steps S2005, S2007, S2009, S2011, and S2012 in FIG. 20.

In the present embodiment, the importance may be set for each of the plurality of states included in the trouble state. In this case, with respect to the state with the importance lower than a predetermined level, the control unit 1360 may cause the notification unit 1350 to make a notification about the trouble state only at the first timing and may not cause the notification unit 1350 to make a notification about the trouble state at the second timing. The control unit 1360 may control the notification unit 350 so that the power consumption is increased for the notification about the trouble state regarding the state with higher importance.

The importance will be more specifically described. The control unit 1360 can change the notification mode according to the importance of the trouble that has occurred in the power supply part 1320, for example. Specifically, for example, when a trouble with the importance higher than the predetermined level has occurred in the power supply part 1320, the control unit 1360 may make a notification about the trouble with a combination of light, vibration and sound. In addition, when a trouble with the importance lower than the predetermined level has occurred, the control unit 1360 may make a notification about the trouble only by light, only by vibration, or only by sound. The control unit 1360 may control so that the power consumption required for a notification about the trouble with high importance is larger than the power consumption required for a notification about the trouble with low importance. This makes it possible for the user and/or the like to easily recognize the occurrence of a trouble in the power supply part 1320 and the content or cause of such a trouble. Furthermore, this makes it possible for the user to easily recognize the importance of the trouble that has occurred in the power supply part 1320. This can prevent the user from overlooking the trouble with high importance that has occurred in the power supply part 1320. Note that the information about the importance of the trouble may be stored in the memory unit 1340.

In the present embodiment, the presence or absence of the second notification according to the content or cause of a trouble may be controlled based on the importance of the trouble. For example, when the high importance is set for the trouble corresponding to the fourth trouble information and the low importance is set for the trouble corresponding to the fifth trouble information, the control unit 1360 may make the second notification about the trouble corresponding to the fourth trouble information and may not make the second notification about the trouble corresponding to the fifth trouble information. This makes it possible to make a notification taking into account the trouble that is strongly desired not to progress. The consumption of electric power stored in the power supply part 1320 can be reduced by omitting the notification about the trouble with low importance.

The present invention is not limited to the above-described embodiments as there are, but may be embodied by modifying constituent elements without departing from the gist of the invention in an implementation stage. In addition, a variety of inventions can be formed by proper combination of a plurality of constituent elements disclosed in the above-described embodiments. For example, some of all the constituent elements disclosed in the above-described embodiments may be deleted. Furthermore, the constituent elements over different embodiments may be combined with one another.

REFERENCE SIGNS LIST

1 . . . Aerosol generation device, 100 . . . Cartridge unit, 110 . . . Storage unit, 120 . . . Supply unit, 130 . . . Load, 140 . . . Atomization unit, 200 . . . Capsule unit, 210 . . . Flavor source, 300 . . . Power supply unit, 310 . . . Power supply button . . . 320 . . . Power supply part, 330 . . . Sensor unit, 331 . . . Microphone capacitor, 331A . . . Diaphragm, 331B . . . Back plate, 332 . . . PTC thermistor, 333 . . . P-type MOSFET, 334 . . . Current measurement sensor, 340 . . . Control unit, 350 . . . Memory unit, 360 . . . Notification unit, AR . . . Air flow path, 1000 . . . Aerosol generation device, 1100 . . . Cartridge unit, 1110 . . . Storage unit, 1120 . . . Supply unit, 1130 . . . Load, 1140 . . . Atomization unit, 1200 . . . Capsule unit, 1210 . . . Flavor source, 1300 . . . Power supply unit, 1310 . . . Power supply button, 1320 . . . Power supply part, 1321 . . . Temperature sensor, 1330 . . . Sensor unit, 1340 . . . Memory unit, D1 to D3 . . . Data, 1350 . . . Notification unit, 1360 . . . Control unit, 1370 . . . Time measurement unit

The invention claimed is:

1. A power supply unit of an aerosol generation device, comprising:
   a first sensor configured to detect an aerosol generation request;
   a second sensor configured to output a value in the second sensor that changes according to an electrical change of the first sensor; and a control unit configured to detect, based on the value, whether the first sensor is in a normal state or an abnormal state.

2. The power supply unit of an aerosol generation device according to claim 1, wherein
the value when the control unit detects the normal state is different from the value when the control unit detects the abnormal state.

3. The power supply unit of an aerosol generation device according to claim 1, wherein
the abnormal state is a state in which an aerosol source is not atomized by an atomization unit to which electric power is supplied from the power supply unit, due to a trouble occurring in the first sensor.

4. The power supply unit of an aerosol generation device according to claim 1, wherein
the normal state is a state in which an aerosol source is capable of being atomized by an atomization unit to which electric power is supplied from the power supply unit.

5. The power supply unit of an aerosol generation device according to claim 1, wherein
a value output from the second sensor is a value of a voltage applied to the second sensor that changes according to a change in a voltage applied to the first sensor, and
the control unit detects, based on the voltage value, whether the first sensor is in the normal state or the abnormal state.

6. The power supply unit of an aerosol generation device according to claim 1, wherein
the second sensor is a PTC thermistor.

7. The power supply unit of an aerosol generation device according to claim 1, wherein
a value output from the second sensor is a value of a current flowing in the second sensor that changes according to a change in a current flowing in the first sensor, and
the control unit detects, based on the current value, whether the first sensor is in the normal state or the abnormal state.

8. The power supply unit of an aerosol generation device according to claim 1, further comprising:
a notification unit,
wherein when detecting the abnormal state, the control unit causes the notification unit to make a notification that the abnormal state is detected.

9. The power supply unit of an aerosol generation device according to claim 1, wherein
when the abnormal state is detected, the control unit causes the power supply unit to undergo a transition from an active state to a sleep state.

10. The power supply unit of an aerosol generation device according to claim 1, further comprising:
a memory unit,
wherein the memory unit stores information indicating the number of times that the control unit has detected the abnormal state.

11. The power supply unit of an aerosol generation device according to claim 10, wherein
the memory unit further stores information indicating a content of the abnormal state detected by the control unit.

12. The power supply unit of an aerosol generation device according to claim 10, wherein
when detecting an instruction to cause the power supply unit to undergo a transition to an active state, the control unit does not cause the power supply unit to undergo a transition to an active state when the number of times is equal to or greater than a predetermined threshold, and causes the power supply unit to undergo the transition to the active state when the number of times is less than the predetermined threshold.

13. The power supply unit of an aerosol generation device according to claim 1, wherein
when the power supply unit is in an active state, the control unit detects whether the first sensor is in the normal state or the abnormal state.

14. A control method for a power supply unit of an aerosol generation device, the method comprising:
acquiring a value in a second sensor that changes according to an electrical change of a first sensor that detects an aerosol generation request; and
detecting, based on the value, whether the first sensor is in a normal state or an abnormal state.

* * * * *